(12) United States Patent
Ye et al.

(10) Patent No.: US 10,377,774 B2
(45) Date of Patent: Aug. 13, 2019

(54) VINBLASTINE DERIVATIVES, PREPARATION METHOD THEREFOR AND APPLICATION THEREOF

(71) Applicant: JINAN UNIVERSITY, Guangdong (CN)

(72) Inventors: Wencai Ye, Guangdong (CN); Heru Chen, Guangdong (CN); Dongmei Zhang, Guangdong (CN); Minfeng Chen, Guangdong (CN); Nanhui Xu, Guangdong (CN)

(73) Assignee: JINAN UNIVERSITY, Guangzhou (CN)

( * ) Notice: Subject to any disclaimer, the term of this patent is extended or adjusted under 35 U.S.C. 154(b) by 0 days.

(21) Appl. No.: 14/785,547

(22) PCT Filed: Mar. 3, 2014

(86) PCT No.: PCT/CN2014/000192
§ 371 (c)(1),
(2) Date: Oct. 19, 2015

(87) PCT Pub. No.: WO2014/169697
PCT Pub. Date: Oct. 23, 2014

(65) Prior Publication Data
US 2016/0068552 A1    Mar. 10, 2016

(30) Foreign Application Priority Data

Apr. 19, 2013  (CN) .......................... 2013 1 0138241
Dec. 30, 2013  (CN) .......................... 2013 1 0738860

(51) Int. Cl.
*C07D 519/04*    (2006.01)
(52) U.S. Cl.
CPC .................................. *C07D 519/04* (2013.01)
(58) Field of Classification Search
None
See application file for complete search history.

(56) References Cited

FOREIGN PATENT DOCUMENTS

| CN | 101108859 A | 1/2008 |
|---|---|---|
| CN | 10386624 A | 3/2009 |
| CN | 101386625 A | 3/2009 |
| CN | 101522679 A | 9/2009 |
| CN | 102558200 A | 7/2012 |
| CN | 103275106 A | 9/2013 |
| JP | 02231493 | 9/1990 |
| WO | 2005055939 | 6/2005 |
| WO | 2005055943 A2 | 6/2005 |
| WO | 2007098091 A2 | 8/2007 |
| WO | 2008098970 A1 | 8/2008 |
| WO | 2009098369 A1 | 8/2009 |
| WO | 2012021907 A2 | 2/2012 |

OTHER PUBLICATIONS

Translation of Xiao (Chinese Doctoral Dissertations Full-text Database, Medicine and Health Sciences, Jun. 15, 2013, 6, pp. 56-62.*
"Diabetic Retinopathy—Prevention—NHS.UK", http://www.nhs.uk/conditions/diabetic-retinopathy/prevention, accessed Apr. 13, 2018.*
"Rheumatoid arthritis—Prevention", http://www.webmd.com/rheumatoid-arthritis/tc/rheumatoid-arthritis-prevention, accessed Apr. 13, 2018.*
Neuss. The Alkaloids, 1990, 37, chapter 6, pp. 229-240.*
Xiao. Chinese Doctoral Dissertations full-text database, Medicine and Health Sciences, Jun. 15, 2013, 6, translation covering pp. 1-3, 5-11, and 58-86 of Xiao.*
Ali, Anticancer Research, 2012, 32, 2999-3006 (Year: 2012).*
PCT/CN2014/000192 International Search Report dated Jun. 10, 2014.
PCT/CN2014/000192 International Search Report and Written Opinion dated Oct. 20, 2015.
Xiao, Xuzhi, reconstitution, Structural Modification and Targeting Design of Diindolyl Alkloids, Chinese Doctoral Dissertations Full-text Database, Medicine and Health Sciences, No. 6, Jun. 15, 2013 (Jun. 15, 2013), pp. 56-82.
Peter B, et al. Curr Opin Genet Dev, 2005, 15: 102-111.
Yun JS, et al. Diabetes Metab J. 2013, 37(4):262-9.
Hirohats, S, et al., Lancet, 1999, 343: 1331.
Ahmed M, et al. Acta Ophthalmol, 2011, 89: e115-e121.

* cited by examiner

*Primary Examiner* — Noble E Jarrell
(74) *Attorney, Agent, or Firm* — JMB Davis Ben-David

(57) ABSTRACT

The present invention provides a new kind of vinca alkaloid derivatives, new applications thereof and preparation methods therefor. The vinca alkaloid derivatives comprise hydrazinolyzed vinca alkaloids and vinca alkaloid dipeptide derivative. The hydrazinolyzed vinca alkaloids are the compounds obtained from the reaction of vinca alkaloids or salts thereof with hydrazinolyzed hydrate; and the vinca alkaloid dipeptide derivatives are the compounds obtained from the condensation of hydrazinolyzed vinca alkaloids with N-benzyloxycarbonylglycyl proline. The present invention provides the uses of the vinca alkaloids derivatives or the pharmaceutical compositions thereof in anti-tumor, preventing or treating diabetic retinopathy, rheumatoid arthritis and serving as angiogenesis inhibitors or vascular disrupting agents.

9 Claims, 9 Drawing Sheets

BX-CCJ

BX-CCRB

BX-CCFN

BX-CCXJ

VINBLASTINE DERIVATIVES, PREPARATION METHOD THEREFOR AND APPLICATION THEREOF

CROSS-REFERENCE TO RELATED APPLICATIONS

The present application is a U.S. National Stage entry under 35 U.S.C. § 371 of International Application No. PCT/CN2014/000192 filed on Mar. 3, 2014, designating the United States of America and published in Chinese on Oct. 23, 2014, which in turn claims priority to Chinese Patent Application No. 201310138241.8 filed on Apr. 19, 2013 and Chinese Patent Application No. 201310738860.0 filed on Dec. 30, 2013, each of which is hereby incorporated by reference in its entirety.

TECHNICAL FIELD

The present invention provides a new kind of vinca alkaloid derivatives and a preparation method therefor and a new application thereof. The present invention belongs to the field of medicine.

BACKGROUND ART

Angiogenesis is a tightly regulated process in various aspects, in the mature mammalian organisms, the physiological angiogenesis only occurs in ovary, uterus and placenta, whereas in other tissues, upon angiogenesis, it will be maintained in a high degree of stability, and regulated by many positive and negative regulatory factors, thereby maintaining a homeostasis state; while the pathological angiogenesis involves in a series of disease processes, such as wound healing, malignant tumor, diabetic retinopathy, rheumatoid arthritis and so on (Peter B, et al. *Curr Opin Genet Dev,* 2005, 15: 102-111).

In the early 1970s, Judah Folkman first proposed that the growth and migration of the malignant tumor are both closely related to the tumor angiogenesis, upon growing up to a diameter of 2~3 mm, a majority of tumors need new blood vessels to supply nutrients and oxygen (Folkman J. *N Engl J Med,* 1971, 285: 1182-1186); as compared with those in the tumor tissues, the vascular endothelial cells in the normal tissues are in a resting state, and the blood vessels are mature and stable; and the vessel cells in the tumor tissues have the following characteristics, such as rapid proliferation, irregular vascular grading, chaotic network, etc. (Dietmar W, et al. *Cancer Treat Rev,* 2011, 37: 63-74). Therefore, the vascular system of the tumor becomes a very important therapeutic target. At present, in most of the literatures, the vascular targeting agents tend to be divided into angiogenesis inhibitors (anti-angiogenic drugs or angiogenesis inhibitors (AIs) and vascular disrupting agents (VDAs) (Patherson D M, et al. *Clin Oncol (R Coll Radiol),* 2007, 19: 443-456). AIs inhibit the tumor neovascularization mainly by inhibiting the matrix degradation, inhibiting the activation of the angiogenic factors and affecting the proliferation of the tumor vascular endothelial cells, etc. (Folkman J. *Nat Rev Drug Discov.* 2007, 6: 273-286). Numerous clinical data have confirmed that, AIs can effectively inhibit the tumor progression, reduce the occurance of tumor metastasis by inhibiting angiogenesis (Gasparini G, et al. *Nat Clin Pract Oncol.* 2005, 2: 562-577); and VDAs can quickly and widely disrupt the formed tumor blood vessels, resulting in a large area of tumor necrosis due to internal ischemia, thereby inhibiting the tumor growth (Philip E T. *Clin Cancer Res,* 2004, 10: 415-427). Therefore, inhibition of tumor angiogenesis and disruption of the formed tumor blood vessels have become effective strategies in developing antitumor drugs.

Diabetic retinopathy is a serious complication of diabetes, which seriously affects the quality of life of the diabetic patient. (Malone J I, et al. *Diabetes Care,* 2001, 24: 522-526; Ramavat P R, et al. *J Clin Diagn Res,* 2013, 7: 1387-1390). Although the exact pathogenesis of diabetic retinopathy is not completely clear at present, some studies have shown that the retinal neovascularization involved in the disease process (Jae S Y, et al. *Diabetes Metab J,* 2013, 37: 262-269). In recent years, it has been found in clinic that bevacizumab, as a receptor antagonist of VEGF (vascular endothelial growth factor), can be used to treat the retinal angiogenesis of the diabetic retinopathic patients, and has achieved a certain effect (Zhao L Q, et al. *Br J Ophthalmol,* 2011, 95: 1216-1222). However, VEGF receptor antagonists can not completely suppress the retinal angiogenesis of the diabetic retinopathic patient (Watanabe D, et al. *N Engl J Med,* 2005, 353: 782-792). Thus, it is of great significance to find more effective drugs for inhibiting the diabetic retinopathy.

On the other hand, rheumatoid arthritis is an autoimmune disease, a refractory disease characterized by eroding cartilage in combination with chronic synovitis, and resulting in the destruction of bone and joint. The pathogenesis of rheumatoid arthritis has not yet been completely clarified hitherto, and there are no specific therapeutics for the same. It has been reported that synovial angiogenesis accompanying with inflammatory cell infiltration is an important pathological feature for the pannus formation in rheumatoid arthritis and the destruction in joint (Lioté F. *Rev Prat,* 1993, 43: 2239-2245; Roccaro A M, et al. *Curr Drug Targets Inflamm Allergy,* 2005, 4: 27-30; Hirohats S, et al. *Lancet,* 1999, 353:1331-1334). Inhibition of the synovial angiogenesis of the rheumatoid arthritis patient has currently become one of the effective strategies for treating rheumatoid arthritis.

Vinca alkaloids comprise vinblastine and vincristine separated from Apocynaceae Catharanthus roseus, and their derivatives vinorelbine and vinflunine, all of them belonging to bisindole alkaloids. Vinblastine (VLB) and vincristine (VCR) are natural original bisindole alkaloids (Beer M T. *Br Emp Cancer Campaign,* 1955, 33: 487-489; Gorman M, et al. *J Am Chem Soc,* 1959, 81: 4745-4746). Pharmacological studies shown that, vinblastine and analogues or derivatives thereof are cytotoxic drugs, which mainly inhibit the polymerization of tubulins, hinder the formation of spindle microtubules and arrest the cell nucleus division in metaphase (Olmsted J B, et al. *Annu Rev Biochem,* 1973, 42: 507-509). Vinblastine and the derivatives thereof have broad-spectrum anticancer activities, and are mainly used to treat Hodgkin's disease and chorionic epithelioma in clinic, and have some therapeutic effects on acute leukemia, breast cancer, ovarian cancer, testicular cancer, head and neck cancer, oropharyngeal cancer, and monocytic leukemia (Wilson L. *Ann NY Acad Sci USA,* 1975, 253: 213-214). In recent years, Angelo Vacca et al have found that vinblastine at a non-toxic dose can significantly inhibit neovasculature at cell levels (Angelo V, et al. Blood, 1999, 94: 4143-4155); the studies of Giannoula Klement et al have shown that the tumor neovascularization can be inhibited by continuous supplying a low dose of vinblastine (Giannoula K, et al. *J Clin Invest,* 2000, 105: R15-24); James Moore, et al have confirmed that vincristine can inhibit the growth of the new tumor blood vessels (James M, et al. *J Pediatr Surg,* 2001, 36: 1273-

1276); on the other hand, Anna Kruczynskia et al have found that vinflunine can inhibit tumor angiogenesis, and at the same time disrupt the formed tumor blood vessels, and also have significant inhibitions on the experimental malignant tumor metastasis (Anna K, et al. *Eur J Cancer*, 2006, 42: 2821-2832). However, the applications and studies of vinca alkaloids on diabetic retinopathy, rheumatoid arthritis, etc., have not been reported yet.

Like many chemotherapy drugs used in clinic, vinca alkaloids have many serious side effects during the treatment of diseases, such as bone marrow suppression, myalgia, nausea and vomiting, and other adverse effects (Magnus P, et al. *J Am Chem Soc,* 1987, 109: 7929-7930), which greatly limit their applications in clinical practice. One of the effective ways to reduce the toxic side effects of such drugs is to make structural modifications on the drugs to produce prodrugs, and make the prodrugs selectively acting on the genes, enzymes, signal transduction factors, etc., of the lesion target cells, by virtue of the molecular biological differences between the lesion tissues and the normal tissues, so as to achieve the purpose of targeted therapy. In recent years, a large number of studies have shown that fibroblast-activation protein α (FAPα) is specifically expressed in the callus tissues and on the surfaces of more than 90% of the tumor tissue activated fibroblasts and pericytes (Teresa R M, et al. Oncogene, 2004, 23: 5435-5446), on the surfaces of osteoarthritis chondrocytes (Jennifer M M, et al. *Arthritis Res Ther,* 2006, 8: R23), and also significantly highly expressed on the surfaces of myofibroblasts in the vitreous retinopathic tissues (Jennifer M M, et al. *Acta Ophthalmol,* 2011, 89: 115-121). In summary, in the present invention, vinca alkaloids are chemically modified to form FAPα enzyme-activated prodrugs, so as to achieve the purposes of targeting, reducing toxiciy and increasing efficiency.

Contents of the Invention

In order to achieve the targeting property of vinca alkaloid drugs, overcome the serious toxic side effects of such drugs in the prior art, and improve the therapeutic effects of the drugs, the present invention provides a new kind of vinca alkaloid derivatives (including hydrazinolyzed vinca alkaloids and vinca alkaloid dipeptide derivatives) and physiologically acceptable salts thereof, the particular technical solutions of the invention are as follows:

The present invention provides a kind of vinca alkaloid dipeptide derivatives or their physiologically acceptable salt thereof, wherein the vinca alkaloid dipeptide derivatives are selected from the structures shown as follows, designated as BX-CCXJ, BX-CCJ, BX-CCRB and BX-CCFN, respectively,

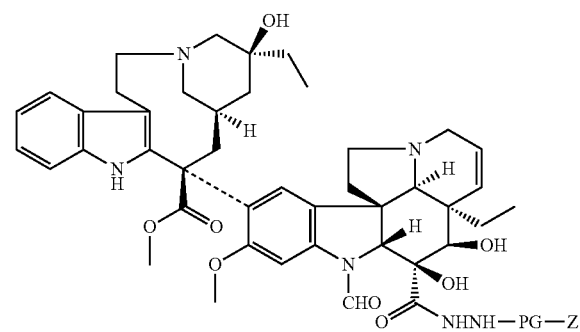

BX-CCXJ

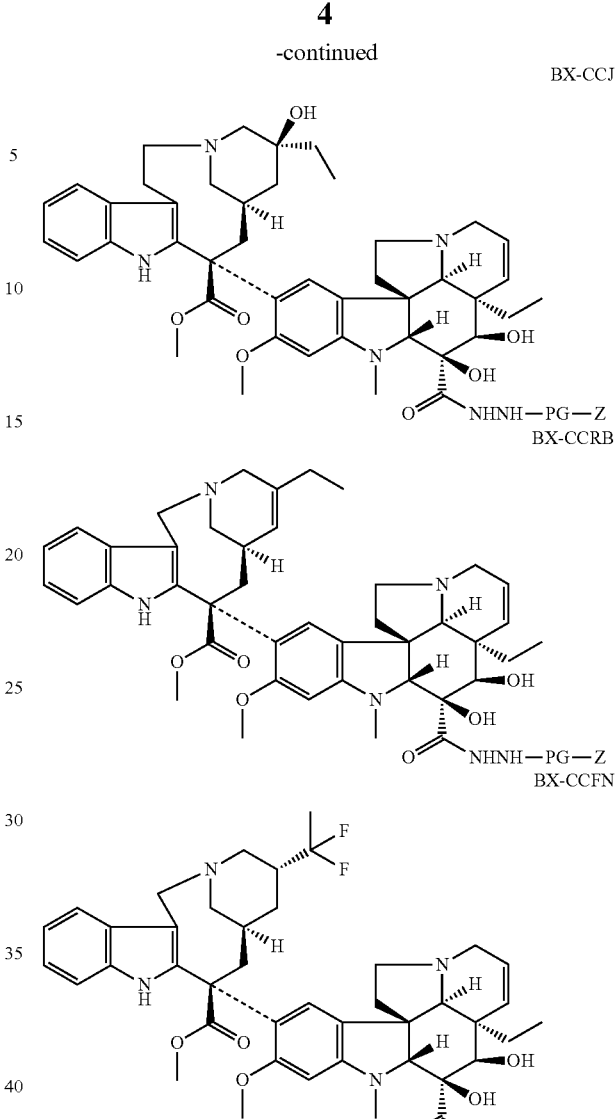

wherein, Z-GP- represents a benzyloxycarbonyl glycyl-prolyl group having the following structure,

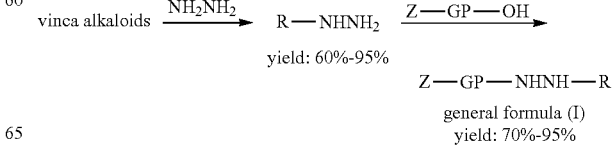

The present invention also provides a method for preparing the vinca alkaloid dipeptide derivatives mentioned above, wherein the synthetic route is as follows

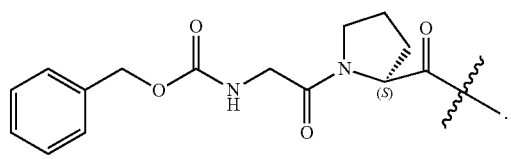

general formula (I)
yield: 70%-95% specifically comprising the following steps:

S1. The vinca alkaloids or their salt thereof are dissolved in an organic solvent, added hydrazinolyzed hydrate, heated with stirring and reacted in dark under nitrogen protection for 10~60 hours; with the reaction temperature controlled at 40° C.~120° C.; after completion of the reaction, separated and purified, thus obtaining the hydrazinolyzed vinca alkaloids (R—NHNH$_2$);

S2. the hydrazinolyzed vinca alkaloids (R—NHNH$_2$), benzyloxycarbonyl glycyl-proline (Z-GP-OH) and a condensing agent, are stirred and reacted in dark at −10° C.~50° C.; after completion of the reaction, quenched with water, separated and purified, thus obtaining the vinca alkaloid dipeptide derivatives (Z-GP-NHNH—R).

As a preferred embodiment, the hydrazinolyzed hydrate in S1 is 40 wt %~80 wt % of hydrazinolyzed hydrate; the molar feeding ratio between the vinca alkaloids and the hydrazinolyzed hydrate is 1:5~1200. The organic solvent in S1 is methanol.

As a preferred embodiment, the condensing agent in S2 is selected from one of or a mixture of more of ethyl chloroformate, 1-ethyl-(3-dimethylaminopropyl) carbodiimide hydrochloride (EDC.HCl), N,N'-diisopropyl carbodiimide (DIC), benzotriazol-1-yl-oxytripyrrolidino-phosphonium hexafluorophosphate (PyBOP) and 1-chloro-N,N',2-trimethylacrylamide.

As a preferred embodiment, the molar feeding ratio among the hydrazinolyzed vinca alkaloids, benzyloxycarbonyl glycyl proline (Z-GP-OH) and the condensing agent in S2 is 1:1.05~3.0:1.05~3.0.

Among them, the vinca alkaloids are selected from vincristine, vinblastine, vinflunine, vinorelbine or their salt thereof; the hydrazinolyzed vinca alkaloids are selected from JJ-CCXJ, JJ-CCJ, JJ-CCRB and JJ-CCFN shown as follows.

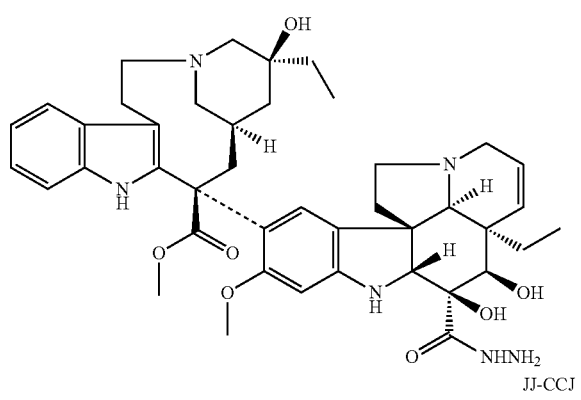

JJ-CCXJ

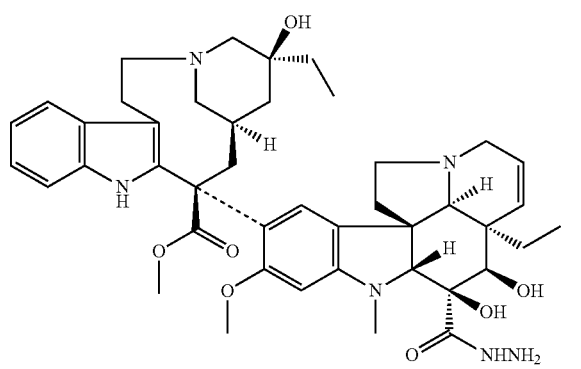

JJ-CCJ

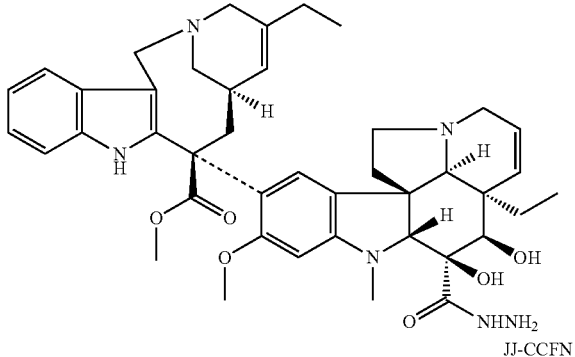

JJ-CCRB

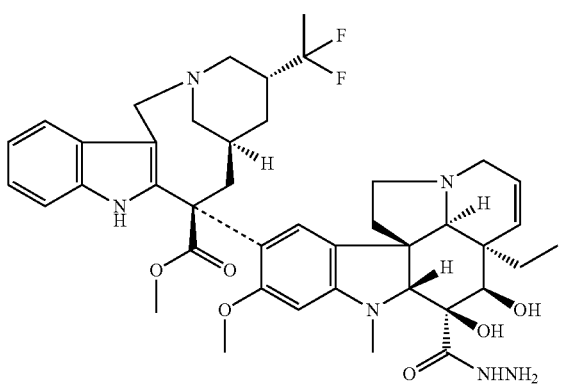

JJ-CCFN

Another object of the present invention is to provide a kind of hydrazinolyzed vinca alkaloids or their physiologically acceptable salt thereof, wherein the hydrazinolyzed vinca alkaloids are selected from JJ-CCXJ, JJ-CCJ, JJ-CCRB and JJ-CCFN as shown above.

The present invention also provides a kind of physiologically acceptable salt of the vinca alkaloid dipeptide derivatives formed from the above mentioned vinca alkaloid dipeptide derivatives and a method for preparing the same.

As a preferred embodiment, the physiologically acceptable salt of the vinca alkaloid-dipeptide derivatives are selected from any one in Table 1:

TABLE 1

| The salt form of the vinca alkaloid dipeptide derivatives |
|---|
| BX-CCJ•sulfate |
| BX-CCXJ•sulfate |
| BX-CCRB•tartrate |
| BX-CCFN•tartrate |

The vinca alkaloid dipeptide derivatives or their physiologically acceptable salt thereof described in the present invention can be present in free state in medical application.

The method for preparing the vinca alkaloid dipeptide derivatives or their physiologically acceptable salt thereof described above, are characterized in that vinca alkaloid dipeptide derivatives are dissolved in an organic solvent containing 1.05~3.0 moles of acid (HA), stirred and reacted at −10° C.~40° C. for 3~20 hours, separated the solid compound, washed, then redissolved the solid compound in water, freeze-dried, thus obtaining the final products.

As a preferred embodiment, the acids are hydrochloric acid, sulfuric acid, acetic acid, tartaric acid or citric acid, and the organic solvent is a solution of methanol and dichloromethane with a volume ratio of 1:1.

The present invention also provides the application of the above mentioned hydrazinolyzed vinca alkaloids, vinca alkaloid dipeptide derivatives or their physiologically acceptable salt thereof in the preparation of the antitumor drugs, preferably, the tumor are stomach cancer, lung cancer, nasopharyngeal cancer, breast cancer, intestinal cancer, liver cancer, leukemia, lymphoma, prostate cancer, cervical cancer, melanoma, ovarian cancer, neuroblastoma, nasopharyngeal carcinoma, nephroblastoma or multidrug resistant tumor.

The present invention also provides the application of the above mentioned hydrazinolyzed vinca alkaloids, vinca alkaloid dipeptide derivatives or their physiologically acceptable salt thereof in the preparation of a medicament in the prevention or treatment of diabetic retinopathy or rheumatoid arthritis.

The present invention also provides the application of the above mentioned hydrazinolyzed vinca alkaloids, vinca alkaloid dipeptide derivatives or their physiologically acceptable salt thereof in the preparation of a medicament in serving as angiogenesis inhibitors or vascular disrupting agents.

The present invention also provides a pharmaceutical composition, comprising the above mentioned vinca alkaloid dipeptide derivatives or their physiologically acceptable salt thereof or the above mentioned hydrazinolyzed vinca alkaloids or their physiologically acceptable salt thereof.

Among them, the above mentioned physiologically acceptable salt can be selected from hydrochloride, sulfate, acetate, tartrate or citrate.

In the above mentioned applications, preferably, the vinca alkaloid dipeptide derivative can be used as a substrate for FAPα-specific hydrolysis.

The present invention has the following beneficial effects as compared with those in the prior art:

(1) The vinca alkaloid dipeptide derivatives described in the present invention can significantly reduce the toxicity in normal cells and the toxicity in vivo, and can be specifically hydrolyzed in vivo and in intro by a specific enzyme, FAPα, which cleaves the dipeptide moiety (Z-GP) and releases hydrazinolyzed vinca alkaloids.

(2) The vinca alkaloid derivatives can significantly inhibit the proliferation of a variety of tumor cell lines in vitro and the tumor growth of tumor-bearing nude mice in vivo.

(3) The vinca alkaloid derivatives of the present invention also have significant effects on inhibiting the angiogenesis and disrupting the formed new blood vessels.

(4) The vinca alkaloid derivatives of the present invention have good inhibitory effects on the invasive capacity, migration capacity and tube formation of HUVECs; and have good inhibitory effects on the angiogenesis of corneal micropocket, the angiogenesis of synovial vessels and the angiogenesis of Matrigel Plug, etc. At the same time, they have disruptive effects on the formed HUVEC tubes, corneal micropocket vessels, synovial vessels and Matrigel Plug vessels.

(5) The in vivo and in vitro drug efficacy tests have shown that the vinca alkaloid derivatives of the present invention can be applied in the treatment and prevention of the diseases, such as malignant tumor, diabetic retinopathy, rheumatoid Arthritis, etc. Particularly, it has been also found in the present invention that the applications of the vinca alkaloid derivatives on the diseases, such as malignant tumor, diabetic retinopathy, rheumatoid arthritis, etc., have better drug efficacies, as compared with those of the vinca alkaloids, and there are significant differences between them in drug efficacy.

(6) The synthetic methods of the present invention have the characteristics of mild conditions, simple procedure, high yield, high purity, good economy and practicality, etc. Particularly, the hydrazinolyzed vinca alkaloids of the present invention can be used as the synthetic intermediates of the vinca alkaloid dipeptide derivatives, moreover they also have good physiological activities, and can be applied in the preparation of the related drugs as the active ingredients.

PARTICULAR EMBODIMENTS

Figure 1:
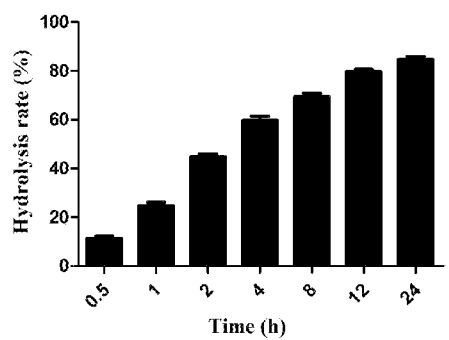
FIG. 1. Enzymatic activity of recombinant humanized FAPα (rhFAPα) on vinca alkaloid dipeptide derivatives FIG. 2. Enzymatic activity of FAPα in tumor tissues on vinca alkaloid dipeptide derivatives FIG. 3. Inhibitory effects of vinca alkaloid derivatives on invasive capacity of HUVECs cells FIG. 4. Inhibitory effects of vinca alkaloid derivatives on migration capacity of HUVECs cells FIG. 5. Inhibitory effects of vinca alkaloid derivatives on tube formation of HUVECs FIG. 6. Disruptive effects of vinca alkaloid derivatives on preformed tubuelar structures of HUVECs FIG. 7. Inhibitory effects of vinca alkaloid derivatives on vessel growth of chick embryo chorioallantoic membrane (CAM)
Figure 1:
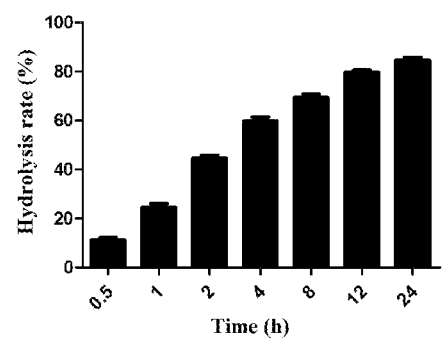
Figure 1:
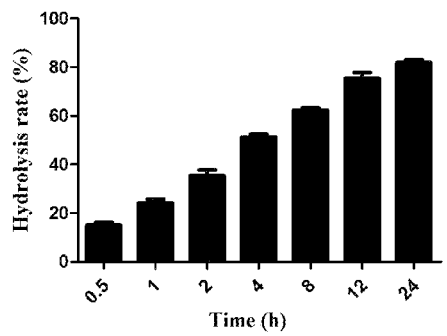
Figure 1:
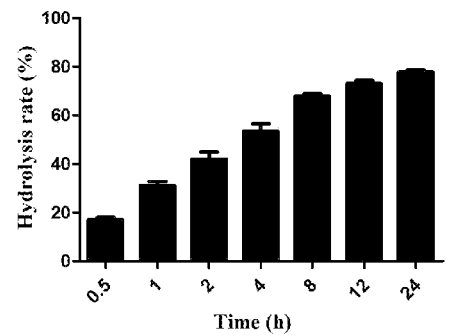

The present invention will be further described in detail below in combination of the examples, but the embodiments of the present invention are not limited thereto.

Example 1. Preparation, Separation and Purification of Vinca Alkaloid Derivatives 1.1.1. Hydrazinolysis of Vinblastine.

To a 35-mL thick wall pressure pipe, 182 mg (0.2 mmol) vinblastine sulphate, following with 8 mL methanol and 0.9 mL 80 wt % hydrazinolyzed hydrate (23 mmol), were added. The mixture was stirred for 5 min by a sonic oscillator and was degassed through $N_2$ bubbling. The container was then covered with plug and protected from light with tinfoil coverage. Then the mixture was stirred over an oil-bath at 60° C. for 24 h. Water was added to terminate the reaction. Multiple extractions with dichloromethane were carried on. After combining all the organic layers, the extract was washed with water and saturated brine, respectively, and dried over anhydrous $Na_2SO_4$. Removal of excess solvent was carried on. The crude residues were then purified by RP-HPLC (Reverse Phase-High Performance Liquid Chromatography) with eluant of $MeOH:H_2O:Et_3N=70:30:0.005$ (in V/V/V), resulted in a slight yellow solid 116 mg with a yield of 76.1%. $^1H$ NMR (300 MHz, $CDCl_3$) δ: 8.19 (s, 1H), 8.03 (s, 1H), 7.51 (d, J=9.0 Hz, 1H), 7.07~7.22 (m, 3H), 6.54 (s, 1H), 6.09 (s, 1H), 5.74~5.88 (m, 2H), 4.13 (m, 2H), 3.84~4.00 (m, 3H), 3.78 (s, 3H), 3.60 (s, 3H), 3.45~3.56 (m, 2H), 3.34 (d, J=6.0 Hz, 1H), 3.29 (d, J=6.0 Hz, 1H), 3.12~3.27 (m, 3H), 2.81~2.93 (m, 3H), 2.78 (s, 3H), 2.61 (s, 1H), 2.39~2.54 (m, 3H), 2.26~2.38 (m, 2H), 1.94~2.08 (m, 2H), 1.64~1.80 (m, 4H), 1.43~1.58 (m, 3H), 1.32~1.45 (m, 4H), 0.81~0.96 (m, 6H); $^{13}C$ NMR (75 MHz, $CDCl_3$) δ: 175.3, 173.4, 158.0, 152.5, 135.0, 131.4, 130.4, 129.3, 123.9, 123.7, 122.5, 122.3, 120.0, 118.9, 118.4, 116.7, 110.5, 93.4, 84.1, 80.5, 73.7, 69.3, 66.4, 64.0, 55.8, 55.7, 53.3, 52.4, 50.4, 50.2, 49.7, 47.7, 45.1, 42.2, 41.0, 40.8, 38.3, 34.5, 32.8, 29.7, 22.6, 8.6, 6.9; ESI-MS (m/z): 769.9[M+H]$^+$. All the data support that the provided compound is hydrazinolyzed vinblastine (JJ-CCJ) with the exact structure as shown below.

JJ-CCJ

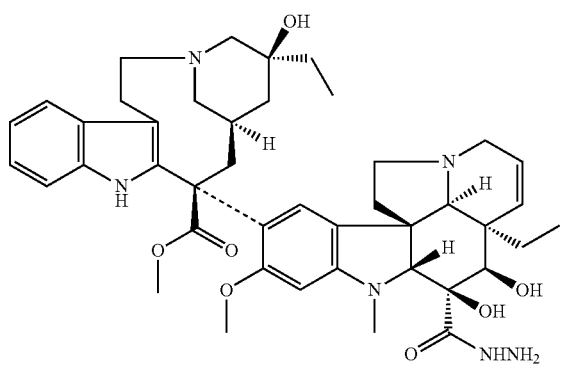

1.1.2. Hydrazinolysis of Vinorelbine.

To a 35-mL thick wall pressure pipe, 185.6 mg (0.2 mmol) vinorelbine tartrate, following 8 mL methanol and 9 mL 80 wt % hydrazinolyzed hydrate (0.23 mol), were added. The mixture was stirred for 5 min by a sonic oscillator and was degassed through $N_2$ bubbling. The container was then covered with plug and protected from light with tinfoil coverage. Then the mixture was stirred over an oil-bath at 52° C. for 60 h. Water was added to terminate the reaction. Multiple extractions with dichloromethane were carried on. After combining all the organic layers, the extract was washed with water and saturated brine, respectively, and dried over anhydrous $Na_2SO_4$. Removal of excess solvent was carried on. The crude residues were then purified by HPLC with eluant of $MeOH:H_2O:Et_3N=70:30:0.005$ (in V/V/V), resulted in a yellow solid 89.8 mg with a yield of 61%. $^1H$ NMR (300 MHz, $CDCl_3$) δ: 8.61 (s, 1H), 8.22 (br s, 1H), 8.02 (d, J=6.0 Hz, 1H), 7.16~7.25 (m, 2H), 6.27 (s, 1H), 6.09 (s, 1H), 5.79~5.92 (m, 2H), 5.71 (d, J=9.0 Hz, 1H), 4.92 (d, J=15.0 Hz, 1H), 4.52 (d, J=15.0 Hz, 1H), 4.19 (d, J=15.0 Hz, 1H), 4.02 (s, 1H), 3.84 (s, 3H), 3.70 (s, 3H), 3.65 (s, 1H), 3.40~3.55 (m, 3H), 3.30 (dd, J=3.0, 15.0 Hz, 1H), 3.10~3.23 (m, 2H), 2.93 (d, J=15.0 Hz, 1H), 2.85 (s, 1H), 2.80 (s, 1H), 2.75 (d, J=3.0 Hz, 1H), 2.60~2.73 (m, 3H), 2.36~2.59 (m, 3H), 2.00~2.14 (m, 4H), 1.88~1.99 (m, 2H), 1.65~1.84 (m, 4H), 1.22~1.34 (m, 4H), 1.10 (t, J=9.0, 3H), 0.84 (t, J=9.0 Hz, 3H); $^{13}C$ NMR (75 MHz, $CDCl_3$) δ: 174.2, 158.1, 152.9, 134.7, 134.4, 131.3, 130.0, 128.2, 124.7, 124.0, 123.4, 123.0, 122.4, 121.4, 119.2, 117.3, 110.6, 104.8, 93.0, 83.7, 73.9, 65.0, 55.7, 54.4, 53.4, 53.3, 53.0, 50.1, 48.9, 47.2, 44.7, 43.5, 42.1, 37.7, 34.5, 31.8, 29.7, 27.6, 27.3, 11.9, 8.5; ESI-MS (m/z): 737.5[M+H]$^+$. All the data support that the provided compound is hydrazinolyzed vinorelbine (JJ-CCRB) with the exact structure as shown below.

JJ-CCRB

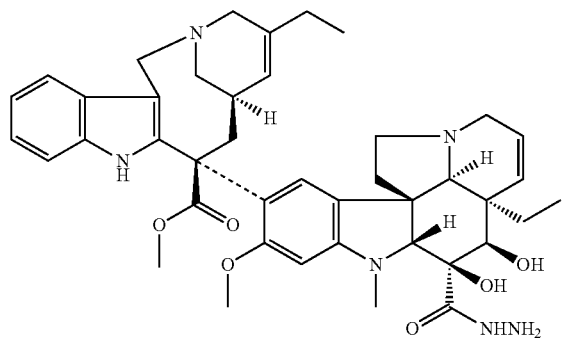

1.1.3. Hydrazinolysis of Vincristine.

To a 100-mL thick wall pressure pipe, 461 mg (0.5 mmol) vincristine sulphate, following 20 mL methanol and 20 mL 80 wt % hydrazinolyzed hydrate (0.51 mol), were added. The mixture was stirred for 5 min by a sonic oscillator and was degassed through $N_2$ bubbling. The container was then cover with plug and protected from light with tinfoil coverage. Then the mixture was stirred over an oil-bath at 60° C. for 24 h. Water was added to terminate the reaction. Multiple extractions with dichloromethane (DCM) were carried on. After combining all the organic layers, the extract was washed with water and saturated brine, respectively, and dried over anhydrous $Na_2SO_4$. Removal of excess solvent was carried on. The crude residues were then purified by RP-HPLC with eluant of $Acetonitrile:H_2O:Et_3N=55:45:0.005$ (in V/V/V), resulted in a slight yellow solid 324 mg with a yield of 86%. $^1H$ NMR (300 MHz, $CDCl_3$) δ: 9.77 (s, 1H), 8.06 (s, 1H), 7.51 (d, J=9.0 Hz, 1H), 7.05~7.19 (m, 3H), 6.60 (s, 1H), 6.20 (s, 1H), 5.76~5.94 (m, 3H), 5.65 (d, J=9.0 Hz, 1H), 5.48 (s, 1H), 4.00 (s, 1H), 3.85~3.96 (m, 1H), 3.83 (s, 1H), 3.72 (s, 3H), 3.58 (s, 3H), 3.25~3.47 (m, 4H), 3.04~3.24 (m, 3H), 2.72~2.88 (m, 3H), 2.35~2.52 (m, 3H), 2.27 (d, J=15.0 Hz, 1H), 2.02~2.15 (m, 2H), 1.98 (s, 3H), 1.79~1.93 (m, 1H), 1.48~1.65 (m, 2H), 1.36~1.48 (m, 2H), 0.8~1.00 (m, 8H); ESI-MS (m/z): 755.6 [M+H]$^+$. All the data support that the provided compound is hydrazinolyzed vincristine (JJ-CCXJ) with the exact structure as shown below.

JJ-CCXJ

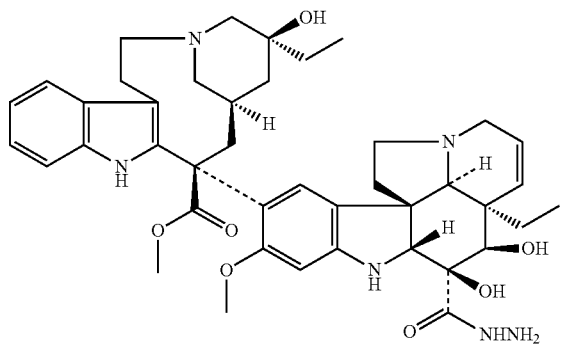

1.1.4. Hydrazinolysis of Vinflunine.

To a 35-mL thick wall pressure pipe, 163.2 mg (0.2 mmol) vinflunine, following by added 8 mL methanol and 9 mL 80 wt % hydrazinolyzed hydrate. The mixture was stirred for 5 min by a sonic oscillator and was degassed through $N_2$ bubbling. The container was then covered with plug and protected from light with tinfoil coverage. Then the mixture was stirred over an oil-bath at 52° C. for 60 h. Water was added to terminate the reaction. Multiple extractions with dichloromethane (DCM) were carried on. After combining all the organic layers, the extract was washed with water and saturated brine, respectively, and dried over anhydrous $Na_2SO_4$. Removal of excess solvent was carried on. The crude residues were then purified by RP-HPLC with eluant of Acetonitrile:$H_2O$:$Et_3N$=55:45:0.005, resulted in a slight yellow solid 80.5 mg with a yield of 52%. $^1H$ NMR (300 MHz, $CDCl_3$) δ: 9.53 (br s, 1H), 8.48 (s, 1H), 8.28 (s, 1H), 7.72 (d, J=6.0 Hz, 1H), 7.18 (m, 3H), 6.32 (s, 1H), 6.08 (s, 1H), 5.55~5.90 (m, 3H), 4.48~4.64 (m, 2H), 4.06 (s, 1H), 3.80 (s, 3H), 3.69 (s, 3H), 3.37~3.45 (m, 3H), 3.23~3.37 (m, 2H), 3.13~3.22 (m, 1H), 2.89~3.12 (m, 2H), 2.79 (s, 3H), 2.66 (d, J=6.0 Hz, 1H), 2.61 (s, 1H), 2.51 (s, 1H), 2.29~2.47 (m, 2H), 1.91~2.05 (m, 3H), 1.79~1.91 (d, J=12.0 Hz, 1H), 1.53~1.78 (m, 6H), 1.22~1.36 (m, 2H), 1.09~1.23 (m, 1H), 0.81 (t, J=9.0 Hz, 3H); $^{13}C$ NMR (75 MHz, $CDCl_3$) δ: 174.7, 173.5, 157.3, 152.5, 134.6, 133.3, 130.2, 128.5, 124.0, 122.8, 122.7, 122.4, 120.0, 119.0, 118.3, 110.6, 109.2, 92.9, 83.8, 80.4, 73.7, 65.5, 55.6, 55.3, 53.4, 53.1, 52.7, 50.2, 49.3, 47.0, 46.3, 44.7, 42.0, 37.9, 33.7, 32.0, 29.9, 28.5, 22.5, 21.5, 8.4; ESI-MS (m/z): 775.4 $[M+H]^+$. All the data support that the provided compound is hydrazinolyzed vinflunine (JJ-CCFN) with the exact structure as shown below.

JJ-CCFN

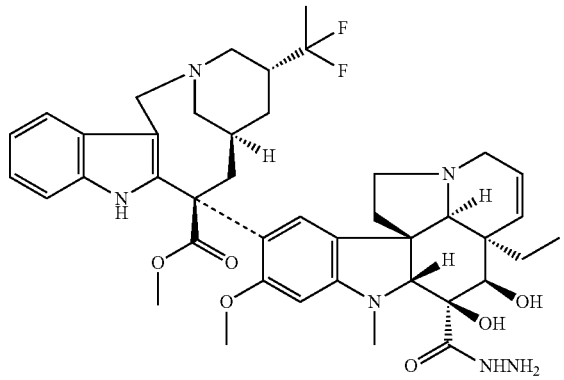

1.2.1. Preparation of Z-GP-NHNH-Vinblastine (BX-CCJ).

36.7 mg (0.12 mmol) of N-carbobenzoxyglycyl proline were dissolved in 5 mL of acetonitrile and sealed with a rubber plug. The solution was put over an ice-bath with stirring for 5 min. Then, 0.031 mL (0.2 mmol) of DIC was added. The reaction was kept on with stirring over ice-bath for 20 min Afterward, 76.8 mg (0.1 mmol) of JJ-CCJ in 1 mL DCM was added slowly. The reaction mixture was then warmed up to room temperature and lasted for 24 h. The reaction was quenched with the addition of water. Multiple extractions with dichloromethane were carried on. After combining all the organic layers, the extract was washed with water and saturated brine, respectively, and dried over anhydrous $Na_2SO_4$. Removal of excess solvent was carried on. The crude residues were then purified by RP-HPLC with eluant of MeOH:$H_2O$:$Et_3N$=70:30:0.005 (in V/V/V), resulted in a slight yellow solid 86.6 mg with a yield of 82.2%. $^1H$ NMR (300 MHz, $CDCl_3$) δ: 8.04 (br, 1H), 7.53 (d, J=9.0 Hz 1H), 7.27~7.38 (m, 5H), 7.05~7.21 (m, 3H), 6.54 (s, 1H), 6.08 (s, 1H), 5.61~5.84 (m, 2H), 5.00~5.20 (m, 2H), 4.63 (d, J=6.0 Hz, 1H), 3.81~409 (m, 4H), 3.76 (s, 3H), 3.60 (s, 3H), 3.56 (s, 2H), 3.25~3.49 (m, 4H), 3.08~3.24 (m, 3H), 3.04 (dd, J=6.0, 15.0 Hz, 1H), 2.86 (s, 2H), 2.81 (s, 3H), 2.60 (s, 1H), 2.37~2.54 (m, 2H), 2.24~2.37 (m, 2H), 1.90~2.10 (m, 4H), 1.58~1.79 (m, 2H), 1.40~1.53 (m, 2H), 1.14~1.39 (m, 8H), 0.81~1.00 (m, 8H); $^{13}C$ NMR (75 MHz, $CDCl_3$) δ: 175.1, 171.2, 169.6, 168.8, 158.0, 156.5, 152.8, 136.5, 134.9, 131.4, 130.3, 129.3, 128.4, 128.0, 124.0, 123.5, 122.4, 122.3, 119.8, 118.9, 118.3, 116.4, 110.5, 93.5, 83.4, 80.8, 73.7, 69.4, 66.8, 66.2, 63.6, 58.8, 55.8, 55.7, 53.4, 53.2, 52.4, 50.3, 49.6, 47.3, 46.3, 45.3, 44.8, 43.4, 42.3, 40.8, 38.6, 34.5, 32.7, 29.6, 29.4, 28.2, 27.4, 24.8, 14.1, 8.7, 8.6, 6.8; ESI-MS (m/z): 1057.9 $[M+H]^+$. All the data support that the provided compound is Z-GP-NHNH-Vinblastine (BX-CCJ) with the exact structure as shown below.

BX-CCJ

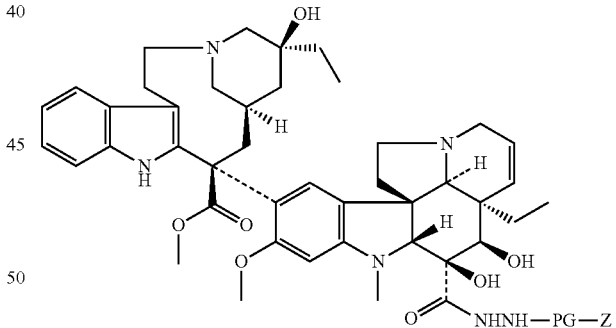

1.2.2. Preparation of Z-GP-NHNH-Vinorelbine (BX-CCRB).

33.7 mg (0.11 mmol) of N-carbobenzoxyglycyl proline (Z-GP-OH) were dissolved in 5 mL of acetonitrile and sealed with a rubber plug. The solution was put over an ice-bath with stirring for 5 min. Then, 0.031 mL (0.2 mmol) of DIC was added. The reaction was kept on with stirring over ice-bath for 20 min, thus reaction mixture A was obtained. Afterward, 73.6 mg (0.1 mmol) of JJ-CCRB was dissolved in 1 mL DCM, dropped into the reaction mixture A, then warmed up to room temperature and lasted for 24 h. The reaction was quenched with the addition of water. Multiple extractions with DCM were carried on. After combining all the organic layers, the extract was washed with water and saturated brine, respectively, and dried over anhydrous $Na_2SO_4$. Removal of excess solvent was carried on. The crude residues were then purified by HPLC with eluant of MeOH:$H_2O$:$Et_3N$=70:30:0.005 (in V/V/V), resulted in a white solid 80.2 mg with a yield of 77%. $^1$H NMR (300 MHz, CDCl$_3$) δ: 8.69 (s, 1H), 8.43 (br, 1H), 7.84 (s, 1H), 7.14~7.40 (m, 9H), 6.41 (s, 1H), 6.32 (s, 1H), 6.08 (s, 1H), 5.79 (s, 2H), 5.60 (d, J=9.0 Hz, 1H), 5.00~5.18 (m, 2H), 4.94 (d, J=15.0 Hz 1H), 4.61 (s, 1H), 4.46 (d, J=12.0 Hz, 1H), 3.88~4.11 (m, 4H), 3.81 (s, 3H), 3.69 (s, 3H), 3.48~3.65 (m, 4H), 3.36 (m, 4H), 2.98~3.27 (m, 8H), 2.87 (m, 1H), 2.83 (s, 3H), 2.67 (m, 2H), 2.52 (t, J=12.0 Hz, 2H), 2.14~2.30 (m, 1H), 1.83~2.14 (m, 6H), 1.66~1.81 (m, 1H), 1.50~166 (m, 1H), 1.30 (t, J=9.0 Hz, 3H), 1.09 (t, J=9.0 Hz, 3H), 0.79 (m, 3H); $^{13}$C NMR (75 MHz, CDCl$_3$) δ: 174.4, 171.1, 170.0, 168.5, 167.9, 157.9, 156.5, 153.0, 136.4, 134.6, 134.2, 131.7, 130.2, 128.2, 128.1, 127.7, 127.6, 124.3, 123.3, 123.1, 122.6, 122.4, 120.6, 118.5, 117.3, 110.5, 105.6, 92.8, 82.8, 80.5, 73.8, 66.4, 64.5, 58.7, 55.6, 54.3, 52.9, 52.7, 52.1, 49.9, 48.9, 46.1, 46.0, 45.1, 44.2, 43.2, 42.8, 42.2, 38.0, 34.4, 31.5, 28.6, 27.4, 27.1, 24.4, 11.7, 8.3, 8.1; ESI-MS (m/z): 1025.6[M+H]$^+$. All the data support that the provided compound is Z-GP-NHNH-Vinorelbine (BX-CCRB) with the exact structure as shown below.

BX-CCRB

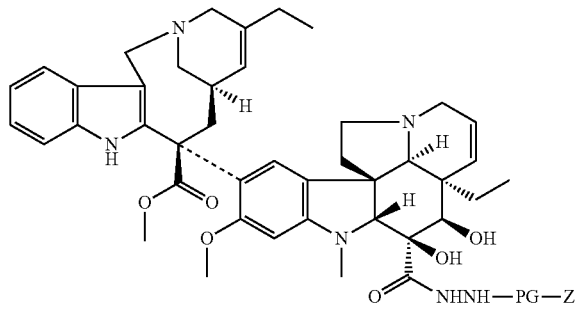

1.2.3. Preparation of Z-GP-NHNH-Vincristine (BX-CCXJ).

137.7 mg (0.45 mmol) of N-carbobenzoxyglycyl proline (Z-GP-OH) were dissolved in 7.5 mL of acetonitrile. The solution was put over an ice-bath with stirring for 5 min. Then, 0.09 mL (0.6 mmol) of DIC was added. The reaction was kept on with stirring over ice-bath for 20 min, thus reaction mixture A was obtained. Afterward, 339.0 mg (0.45 mmol) of JJ-CCXJ was dissolved in 4.5 mL DCM, dropped into the reaction mixture A, then warmed up to room temperature and lasted for 24 h. The reaction was quenched with addition of water. Multiple extractions with DCM were carried on. After combining all the organic layers, the extract was washed with water and saturated brine, respectively, and dried over anhydrous $Na_2SO_4$. Removal of excess solvent was carried on. The crude residues were then purified by HPLC with eluant of MeOH:$H_2O$:$Et_3N$=80:20:0.005 (in V/V/V), resulted in a slight yellow solid 286.1 mg with a yield of 61%, which was named as compound B.

Afterward, 208 mg (0.2 mmol) of compound B was dissolved in 3 mL of DCM and added appropriate amount of acetic formic anhydride solution, which was prepared by mixing 1.1 mol acetic anhydride and 0.5 mL formic acid solution, fully stirred with a proportion of 11:5. The mixture was stirred at room temperature for 2 h. Then, excess reagent was removed by evaporation. The crude residues were then purified by RP-HPLC with eluant of MeOH:$H_2O$:$Et_3N$=65:35:0.005, resulted in a slight yellow solid 70.3 mg with a yield of 32.9%. $^1$H NMR (300 MHz, CD$_3$OD) δ: 8.50 (m, 1H), 7.43 (d, J=6.0 Hz, 2H), 7.20~7.57 (m, 11H), 7.15 (d, J=6.0 Hz, 1H), 7.08 (t, J=6.0 Hz, 2H), 7.00 (t, J=6.0 Hz, 2H), 6.54 (s, 1H), 6.27 (s, 1H), 5.80 (m, 2H), 5.56~5.72 (m, 2H), 5.00~5.14 (m, 4H), 4.42~461 (m, 2H), 3.90~410 (m, 9H), 3.77~3.89 (m, 3H), 3.72~3.75 (m, 1H), 3.73 (s, 3H), 3.61~3.68 (m, 4H), 3.60 (s, 3H), 3.49~3.57 (m, 3H), 3.44 (d, J=6.0 Hz, 1H), 3.35~3.41 (m, 1H), 3.29~3.33 (m, 4H), 3.16~3.29 (m, 6H), 3.00~3.15 (m, 3H), 2.70~2.87 (m, 5H), 2.63 (d, J=12.0 Hz, 1H), 2.39~2.52 (m, 4H), 2.21~2.38 (m, 4H), 2.05~2.21 (m, 7H), 1.92~2.05 (m, 4H), 1.80~2.02 (m, 2H), 1.62~174 (m, 1H), 1.44~161 (m, 4H), 1.20~144 (m, 13H), 0.66~100 (m, 17H); $^{13}$C NMR (75 MHz, CD$_3$OD) δ: 177.3, 174.0, 173.9, 173.3, 170.3, 170.2, 159.3, 158.9, 158.5, 151.4, 138.1, 136.9, 136.5, 132.1, 131.8, 131.1, 130.4, 130.2, 129.4, 129.0, 128.9, 128.8, 126.4, 125.4, 125.2, 124.0, 123.3, 120.6, 119.9, 119.1, 118.2, 117.6, 112.0, 111.3, 102.4, 94.3, 82.8, 81.7, 75.7, 75.0, 69.5, 69.3, 69.0, 67.7, 64.0, 60.4, 60.3, 60.1, 57.5, 56.9, 56.6, 56.3, 54.4, 54.0, 53.0, 52.9, 51.9, 51.8, 47.6, 44.7, 44.1, 43.5, 41.1, 40.9, 35.8, 33.6, 33.3, 33.0, 30.7, 30.5, 30.4, 27.7, 25.8, 23.7, 14.4, 9.0, 7.3; ESI-MS (m/z): 1071.5 [M+H]$^+$. All the data support that the provided compound is Z-GP-NHNH-Vincristine (BX-CCXJ) with the exact structure as shown below.

BX-CCXJ

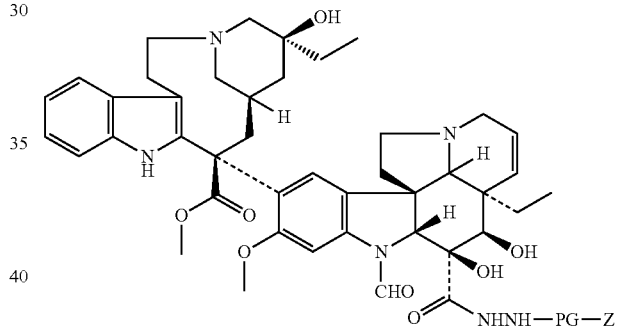

1.2.4. Preparation of Z-GP-NHNH-Vinflunine (BX-CCFN).

30.6 mg (0.1 mmol) of N-carbobenzoxyglycyl proline (Z-GP-OH) were dissolved in 5 mL of acetonitrile and sealed with a rubber plug. The solution was put over an ice-bath with stirring for 5 min. Then, 0.031 mL (0.2 mmol) of DIC was added. The reaction was kept on with stirring over ice-bath for 20 min Afterward, 77.4 mg (0.1 mmol) of JJ-CCFN in 1 mL DCM was added slowly. The reaction mixture was then warmed up to room temperature and lasted for 24 h. The reaction was quenched with the addition of water. Multiple extractions with DCM were carried on. After combining all the organic layers, the extract was washed with water and saturated brine, respectively, and dried over anhydrous $Na_2SO_4$. Removal of excess solvent was carried on. The crude residues were then purified by HPLC with eluant of MeOH:$H_2O$:$Et_3N$=75:25:0.005 (in V/V/V), resulted in a slight yellow solid 77.2 mg with a yield of 74%. $^1$H NMR (300 MHz, CDCl$_3$) δ: 8.54 (s, 1H), 7.73 (d, J=6.0 Hz, 1H), 7.26~7.38 (m, 5H), 7.18 (m, 3H), 6.31 (s, 1H), 6.07 (s, 1H), 5.79 (dd, J=3.0, 9.0 Hz, 1H), 5.64 (d, J=12.0 Hz, 1H), 5.01~5.16 (m, 2H), 4.44~4.75 (m, 2H), 3.85~4.13 (m, 2H), 3.79 (s, 3H), 3.68 (s, 3H), 3.51~3.65 (m, 2H), 3.31~3.50 (m, 3H), 3.26 (dd, J=3.0, 15 Hz, 1H), 3.07~3.19 (m, 1H), 2.90~3.07 (m, 3H), 2.82 (s, 3H), 2.78 (s, 1H), 2.64

(dd, J=6.0, 15.0 Hz, 1H), 2.55 (s, 1H), 2.33~2.49 (m, 2H), 1.65~1.73 (m, 2H), 1.59~1.68 (m, 3H), 1.31~1.43 (m, 1H), 1.20~1.31 (m, 5H), 1.06~1.20 (m, 2H), 0.82~0.92 (m, 1H), 0.80 (t, J=9.0 Hz, 1H); $^{13}$C NMR (75 MHz, CDCl$_3$) δ: 174.6, 173.3, 171.2, 170.0, 168.6, 157.8, 156.5, 155.7, 153.0, 136.4, 134.6, 133.5, 130.3, 128.5, 128.4, 127.9, 127.8, 124.3, 122.9, 122.5, 122.4, 120.1, 118.8, 118.3, 93.1, 83.1, 80.7, 73.8, 66.7, 65.3, 58.7, 55.6, 55.3, 53.1, 52.7, 50.2, 49.5, 49.4, 49.2, 46.4, 46.3, 45.8, 45.0, 44.5, 43.3, 42.3, 38.2, 33.6, 32.0, 29.6, 28.6, 28.1, 24.7, 22.5, 8.6, 8.3; ESI-MS (m/z): 1063.4 [M+H]$^+$. All the data support that the provided compound is Z-GP-NHNH-Vinflunine (BX-CCFN) with the exact structure as shown below.

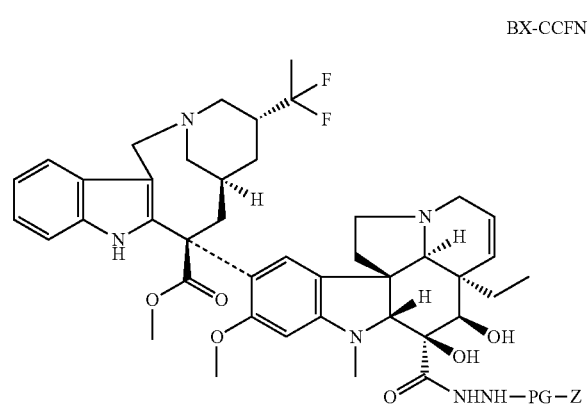

BX-CCFN

1.3.1. Preparation of BX-CCJ Sulphate.

106.0 mg (0.1 mmol) of BX-CCJ were dissolved in 12 mL of 0.01 mmol/L sulphuric acid in 1:1 methanol/dichloromethane solution. The solution was stirred at 0° C. for 3 h. Then removal of excess reagents was carried on at room temperature by vacuum evaporation. The resulted solid was washed with cold ether for triple times and removed diethyl ether by centrifugation. The solid compounds was composited and then re-dissolved in water. After lyophilization, 111.4 mg of BX-CCJ sulphate were collected with a yield of 96.2%.

1.3.2. Preparation of BX-CCRB Tartrate.

102.5 mg (0.1 mmol) of BX-CCRB were dissolved in 15 mL of 0.01 mmol/L tartaric acid in 1:1 methanol/dichloromethane solution. The solution was stirred 0° C. for 3 h. Then removal of excess reagents was carried on at room temperature by vacuum evaporation. The resulted solid was washed with cold ether for triple times and removed diethyl ether by centrifugation. The solid compounds was composited and then re-dissolved in water. After lyophilization, 115.1 mg of BX-CCRB tartrate were collected with a yield of 98%.

Example 2. In Vitro Cell Growth Inhibitory Activities of Vinca Alkaloid Derivatives Experimental method: Cell lines (human non-small-cell lung cancer cell line A549, human colon cancer cell line LOVO, human nasopharyngeal carcinoma cell line CNE-2, human liver cancer cell line HepG2, human cervical carcinoma cell line Hela, human breast cancer cell lines MCF-7 and MDA-MB-231, human gastric carcinoma cell line NCI-N87, human prostatic cancer cell lines PC-3 and DU145, human leukemia cell line K562, human melanoma cell line A375, human neuroblastoma cell line SH-SY5H, human promyelocytic leukemia cell line HL-60, 5-FU-resistant human hepatocellular carcinoma cell line BEL-7402/5-Fu, doxorubicin-resistant hepatocellular carcinoma cell line HepG2/ADM, doxorubicin-resistant human breast cancer cell lines MCF-7/ADR) at logarithmic phase were resuspended in RPMI 1640 medium (containing 10% fetal bovine serum, 100 U/mL penicillin-streptomycin). Then, 100 μL of cells (cell concentration was 5×10$^5$/mL) were seeded into 96 wells plate. After 24 h incubation at 37° C. with 5% CO$_2$, tested compounds were added (the control group without compound) for an additional 72 h incubation. After that, 30 μL of MTT [3-(4,5-Dimethylthiazol-2-yl)-2,5-diphenyltetrazolium bromide] solution (5 mg/mL) was added into each well and incubated for another 4 h at 37° C. and then the formazan crystals were solubilized with 100 μL DMSO. Finally, absorbance of each well was determined at 570 nm by a microplate reader (Thermo).

Cell growth inhibition rates were measured using the following formula:

$$\text{Inhibition rates (\%)} = (1 - OD \text{ value of drug group}/OD \text{ value of control group}) \times 100\%$$

The standard curve was drew with compound concentrations as the abscissa and cell growth inhibition rates as the ordinate. The concentration required to inhibit cell growth by 50% (IC$_{50}$) was calculated from survival curves.

Results: From table 2-1 and 2-2, vinca alkaloids, hydrazinolyzed vinca alkaloids and of vinca alkaloid dipeptide derivatives all had a broad spectrum of anticancer activity. At FAPα negative expressed tumor cell lines, cell growth inhibitory activities were similar among vinca alkaloids and hydrazinolyzed vinca alkaloids and superior to their vinca alkaloid dipeptide derivatives. Besides, the cell growth inhibitory activities were similar among hydrazinolyzed vinca alkaloids and of vinca alkaloid dipeptide derivatives at FAPα positive expressed LOVO cells. These results showed that the vinca alkaloid dipeptide derivatives could be hydrolied by FAPα enzyme, and corresponding hydrazinolyzed vinca alkaloids were produced.

TABLE 2-1

Detection of inhibitory effects of vinca alkaloid derivatives on growth of multiple tumor cell lines by MTT assay

| Tumor cell | IC$_{50}$ (nM) | | | | | |
|---|---|---|---|---|---|---|
| | Vinblastine | JJ-CCJ | BX-CCJ | Vinorelbine | JJ-CCRB | BX-CCRB |
| A549 | 2.31 ± 0.13 | 6.43 ± 2.42 | 62.11 ± 3.87 | 14.54 ± 1.07 | 73.06 ± 2.36 | 114.81 ± 5.23 |
| LOVO | 1.20 ± 0.24 | 32.92 ± 6.39 | 44.79 ± 8.15 | 7.86 ± 0.16 | 120.54 ± 10.33 | 123.07 ± 11.45 |
| CNE-2 | 1.03 ± 0.07 | 7.14 ± 0.16 | 52.67 ± 3.01 | 9.03 ± 0.35 | 100.38 ± 5.90 | 210.32 ± 5.78 |
| HepG2 | 3.07 ± 0.12 | 12.44 ± 0.72 | 46.84 ± 1.17 | 8.34 ± 0.53 | 89.31 ± 0.71 | 167.22 ± 4.37 |
| Hela | 4.34 ± 0.36 | 14.50 ± 1.81 | 56.77 ± 3.08 | 11.38 ± 1.04 | 61.32 ± 3.12 | 181.53 ± 2.36 |

TABLE 2-1-continued

Detection of inhibitory effects of vinca alkaloid derivatives on growth of multiple tumor cell lines by MTT assay

| Tumor cell | IC$_{50}$ (nM) | | | | | |
|---|---|---|---|---|---|---|
| | Vinblastine | JJ-CCJ | BX-CCJ | Vinorelbine | JJ-CCRB | BX-CCRB |
| MCF-7 | 3.67 ± 1.34 | 23.93 ± 3.07 | 107.88 ± 4.23 | 49.47 ± 2.01 | 121.59 ± 5.75 | 237.76 ± 8.37 |
| MDA-MB-231 | 0.81 ± 0.35 | 5.99 ± 3.29 | 64.22 ± 4.57 | 39.69 ± 5.79 | 100.89 ± 7.65 | 180.69 ± 8.10 |
| NCI-N87 | 2.23 ± 0.43 | 17.37 ± 2.20 | 103.49 ± 8.87 | 35.78 ± 6.57 | 89.02 ± 3.34 | 244.07 ± 9.33 |
| PC-3 | 1.56 ± 0.39 | 6.27 ± 0.61 | 71.10 ± 1.97 | 23.67 ± 4.31 | 65.89 ± 3.05 | 269.76 ± 2.03 |
| DU-145 | 0.78 ± 0.31 | 5.33 ± 0.60 | 57.30 ± 2.07 | 19.90 ± 0.57 | 60.44 ± 7.01 | 218.74 ± 6.29 |
| K562 | 0.72 ± 0.20 | 3.67 ± 0.79 | 11.69 ± 3.04 | 12.25 ± 0.54 | 49.74 ± 3.39 | 108.77 ± 4.66 |
| A375 | 3.24 ± 0.39 | 4.56 ± 0.57 | 49.54 ± 4.53 | 5.64 ± 0.95 | 20.37 ± 2.85 | 120.35 ± 14.51 |
| SH-SY5H | 6.13 ± 0.51 | 6.24 ± 1.31 | 59.83 ± 6.42 | 4.78 ± 0.84 | 32.94 ± 3.27 | 165.74 ± 15.62 |
| HL-60 | 5.21 ± 0.84 | 8.65 ± 1.28 | 85.49 ± 9.57 | 8.68 ± 1.35 | 46.82 ± 5.41 | 208.41 ± 18.43 |
| BEL-7402/5-Fu | 25.77 ± 3.01 | 80.34 ± 7.53 | 179.44 ± 8.87 | 36.09 ± 4.78 | 143.13 ± 8.57 | 325.44 ± 11.74 |
| HepG2/ADM | 10.07 ± 1.12 | 43.90 ± 3.77 | 146.43 ± 5.47 | 24.40 ± 3.82 | 182.06 ± 4.38 | 437.09 ± 14.43 |

TABLE 2-2

Detection of inhibitory effects of vinca alkaloid derivatives on growth of multiple tumor cell lines by MTT assay

| Tumor cell | IC$_{50}$ (nM) | | | | | |
|---|---|---|---|---|---|---|
| | Vinflunine | JJ-CCFN | BX-CCFN | Vincristine | JJ-CCXJ | BX-CCXJ |
| A549 | 137.11 ± 4.10 | 206.34 ± 6.79 | 334.59 ± 7.31 | 1.32 ± 0.03 | 4.34 ± 0.42 | 47.71 ± 2.64 |
| LOVO | 145.78 ± 7.21 | 312.84 ± 7.64 | 319.78 ± 8.51 | 0.74 ± 0.09 | 24.30 ± 1.09 | 24.90 ± 1.78 |
| CNE-2 | 67.43 ± 3.42 | 198.35 ± 7.71 | 309.41 ± 5.78 | 1.51 ± 0.76 | 8.37 ± 2.70 | 40.15 ± 2.09 |
| HepG2 | 32.07 ± 2.17 | 103.21 ± 6.37 | 299.10 ± 7.64 | 0.97 ± 0.12 | 12.27 ± 1.96 | 33.43 ± 2.01 |
| Hela | 56.66 ± 4.47 | 132.02 ± 6.67 | 430.2 ± 10.11 | 2.33 ± 0.77 | 23.56 ± 2.97 | 55.34 ± 1.90 |
| MCF-7 | 77.03 ± 2.74 | 303.89 ± 9.44 | 605.71 ± 11.47 | 2.74 ± 0.36 | 26.88 ± 4.38 | 73.21 ± 3.66 |
| MDA-MB-231 | 61.29 ± 7.44 | 332.62 ± 12.47 | 614.44 ± 9.29 | 1.03 ± 0.22 | 7.37 ± 1.18 | 57.32 ± 3.36 |
| NCI-N87 | 57.49 ± 3.95 | 132.60 ± 6.70 | 430.34 ± 10.39 | 0.87 ± 0.26 | 10.73 ± 1.78 | 43.17 ± 3.53 |
| PC-3 | 31.14 ± 5.34 | 98.34 ± 3.19 | 317.45 ± 31.27 | 2.93 ± 0.37 | 27.07 ± 2.18 | 88.91 ± 6.84 |
| DU-145 | 22.31 ± 1.67 | 90.75 ± 5.45 | 289.43 ± 28.77 | 1.17 ± 0.31 | 18.44 ± 3.67 | 76.90 ± 4.55 |
| K562 | 19.27 ± 2.48 | 55.87 ± 7.59 | 229.31 ± 6.60 | 1.07 ± 0.33 | 12.08 ± 1.67 | 44.90 ± 3.28 |
| A375 | 39.84 ± 5.29 | 132.28 ± 9.51 | 528.41 ± 34.79 | 0.95 ± 0.16 | 15.62 ± 2.38 | 54.82 ± 8.41 |
| SH-SY5H | 52.37 ± 6.81 | 159.46 ± 20.38 | 459.36 ± 13.48 | 1.34 ± 0.21 | 18.69 ± 2.54 | 61.72 ± 6.14 |
| HL-60 | 41.75 ± 6.85 | 197.54 ± 19.52 | 725.67 ± 98.21 | 1.81 ± 0.17 | 32.47 ± 3.51 | 72.85 ± 4.59 |
| BEL-7402/5-Fu | 45.66 ± 3.98 | 166.48 ± 5.77 | 389.64 ± 15.70 | 22.69 ± 3.37 | 106.44 ± 5.87 | 326.45 ± 13.32 |
| HepG2/ADM | 67.14 ± 4.39 | 276.89 ± 9.67 | 603.71 ± 17.88 | 7.78 ± 2.01 | 44.90 ± 3.67 | 134.88 ± 5.54 |
| MCF-7/ADR | 154.39 ± 3.95 | 713.46 ± 25.57 | 907.93 ± 20.18 | 9.67 ± 2.20 | 63.23 ± 7.74 | 168.80 ± 5.67 |

Example 3. In Vitro Cytotoxicity of Vinca Alkaloid Derivatives on Normal Cell Lines Experimental method: In vitro cytotoxicities of vinca alkaloids, hydrazinolyzed vinca alkaloids and vinca alkaloid dipeptide derivatives on human normal liver cells LO2 and human umbilical vein endothelial cells HUVEC were detected according to the method of Example 2.

Results: The cytotoxicity of hydrazinolyzed vinca alkaloids and vinca alkaloid dipeptide derivatives on LO2 and HUVEC were much smaller than of the corresponding vinca alkaloids (Table 3). The results showed that cytotoxicity of the targeted compounds were declined dramatically.

TABLE 3

Cytotoxicity of vinca alkaloid derivatives on normal cell lines tested by MTT assay

| Compound | IC$_{50}$ (nM) | |
|---|---|---|
| | HUVEC | LO2 |
| Vinblastine | 0.76 ± 0.13 | 0.34 ± 0.07 |
| JJ-CCJ | 36.07 ± 1.00 | 20.10 ± 0.97 |
| BX-CCJ | 128.88 ± 1.34 | 96.27 ± 1.11 |
| Vinorelbine | 1.13 ± 0.56 | 0.97 ± 0.08 |
| JJ-CCRB | 44.02 ± 2.27 | 31.46 ± 2.29 |
| BX-CCRB | 166.64 ± 8.87 | 183.12 ± 5.51 |
| Vinflunine | 1.53 ± 0.33 | 0.79 ± 0.30 |
| JJ-CCFN | 64.43 ± 5.04 | 28.87 ± 2.76 |
| BX-CCFN | 269.90 ± 7.70 | 301.31 ± 14.30 |
| Vincristine | 0.42 ± 0.09 | 0.21 ± 0.05 |
| JJ-CCXJ | 48.64 ± 2.13 | 22.59 ± 2.08 |
| BX-CCXJ | 175.70 ± 5.51 | 100.70 ± 9.02 |

Example 4. Experiment on Recombinant Humanized FAPα (rhFAPα)-Specific Enzymolysis of Vinca Alkaloid Dipeptide Derivatives Experimental method: HPLC chromatographic conditions were as follows: high-performance liquid chromatograph (HPLC): Agilent 1200; chromatographic column: Cosmosil $C_{18}$ reverse phase chromatographic column (4.6×250 mm², 5 μm); mobile phase[0 min, 55% methanol and 45% water (containing 2 mM ammonium formate); 10 min, 65% methanol and 35% water (containing 2 mM ammonium formate); 15 min, 75% methanol and 25% water (containing 2 mM ammonium formate); 30 min, 85% methanol and 15% water (containing 2 mM ammonium formate); 40 min, 85% methanol and 15% water (containing 2 mM ammonium formate)]; flow rate: 1 mL/min; determine wavelength: 254 nm; sample size: 2 μL. The standard curve of vinca alkaloid dipeptide derivatives was established as follows: vinca alkaloid dipeptide derivatives were dissolved in the buffer of the enzymatic hydrolysis reaction (50 mM Tris-HCl, 1.0 M NaCl, pH7.4) with five different concentrations (6.25, 12.5, 25, 50, 100 μM). The standard curve was drew with peak area as the ordinate (Y) and compound concentrations (μM) as the abscissa (X). The experiment was repeated three times. 50 μM vinca alkaloid dipeptide derivatives was incubated with rhFAPα (5 μg/ml) buffer of the enzymatic hydrolysis reaction at 37° C. water bath. Then the supernatants were collected and detected at 0, 0.5, 1, 2, 4, 8, 12 and 24 h, enzymatic hydrolysate was measured by HPLC and the enzymolysis rate was calculated (A: BX-CCJ; B: BX-CCRB; C: BX-CCFN; D: BX-CCXJ).

Results: Results showed that vinca alkaloid dipeptide derivatives were hydrolysed by recombinant humanized FAPα enzyme in a time-dependent manner (FIG. 1).

Example 5. Experiment on Tumor Tissues FAPα (rhFAPα)-Specific Enzymolysis of Vinca Alkaloid Dipeptide Derivatives Experimental method: 21 days after the xenografts implantation, the mice were killed by dislocation method after anesthesiaed by $CO_2$. Then tumors were stripped, washed with saline and cleaned off periadventitial fat, followed by soaking up the surface water with filter. Besides, about 2 g tumor tissues were cut into small tissue pieces, transferred to glass homogenate, then 10 mL enzyme buffer was added. The homogenate was collected and filtered by 200-mesh sieve, and then 10 mL homogenate was mixed with 10 μL 50 mM vinca alkaloid dipeptide derivatives with the final concentration 50 μM, reacted in 37° C. water bath. 2 mL homogenate was collected at 0, 2, 8, 12 and 24 h, and transferred to 15 mL contrifuge tube, then 5 mL extracting agent (acetonitrile/dichloroethane=1:4) was added, following by vortexed for 1 min and centrifuged with 2500 rpm for 5 min. The lower organic phase to blow dry under nitrogen, and the residue was solubilized with 200 μL methanol, then filtered by 0.22 μm filter membrane. Finally, enzymatic hydrolysate was measured by HPLC and enzymolysis rate was calculated (A: BX-CCJ; B: BX-CCRB; C: BX-CCFN; D: BX-CCXJ).

Figure 2:
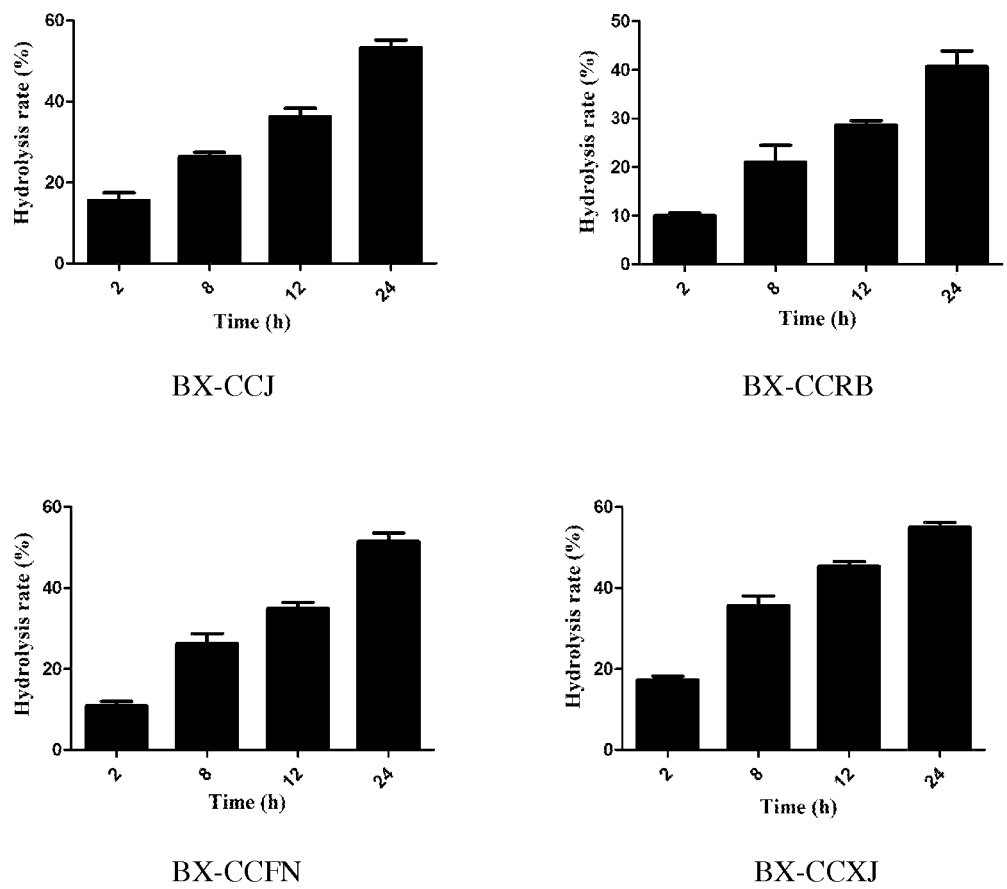

Results: Results showed that vinca alkaloid dipeptide derivatives were hydrolysed by tumor tissues FAPα enzyme in tumor homogenates in a time-dependent manner (FIG. 2).

Example 6. Acute Toxicity Test of Vinca Alkaloid Dipeptide Derivatives

Experimental method: Kunming mice were purchased from Guangdong Medical Experimental Animal Center, weighing 18-22 g, then randomly divided into several groups with 10 mice in each group. Different concentrations of VLB and vinca alkaloid dipeptide derivatives were injected intraperitoneally. Finally, the median lethal dose ($LD_{50}$) was calculated according to the surviving animals.

$LD_{50}$ was measured using the following formula:

$LD_{50}$ (mg/kg)=The median lethal dose/body weight

Results: Results showed that the $LD_{50}$ of BX-CCJ, BX-CCRB, BX-CCFN and BX-CCXJ were 10 mg/kg, 12 mg/kg, 15 mg/kg and 10 mg/kg respectively. But, 4 mg/kg of VLB caused half of the mice dead.

Example 7. In Vivo Assay of Vinca Alkaloid Derivatives on Tumor Xenograft Models Experimental method: The MDA-MB-231 cells at logarithmic phase were digested and washed twice with PBS. Then, 100 μL cells (1×10⁷) were inoculated subcutaneously on the backs of female BALB/nu/nu mice. After tumors grew to 70~100 mm³, the mice were divided randomly into saline group (control group), vinca alkaloids groups (VLB, CCRB, CCFN, CCXJ) and vinca alkaloid derivatives groups (JJ-CCJ, BX-CCJ, JJ-CCRB, BX-CCRB, JJ-CCFN, BX-CCFN, JJ-CCXJ and BX-CCXJ), with six mice per group. 1 mg/kg drugs were injected intraperitoneally every two days, meanwhile body weight and tumor sizes were measured. Experiment was ended after 8 times of drug administration, then tumor and organs were stripped. Tumor volumes were measured using the following formula: $V=\frac{1}{2}(ab^2)$, whereas a refers to the longest diameter and b is the shortest diameter.

Tumor xenograft models of HepG2, LOVO, K562 and HL-60 cell lines were performed as the method described above.

Results: 1 mg/kg of vinca alkaloids and vinca alkaloid derivatives all dramatically inhibited tumor xenograft models of MDA-MB-231, HepG2, LOVO, K562 and HL-60 cell lines (Table 4-8). The toxicity of vinca alkaloid dipeptide derivatives was far below vinca alkaloids and hydrazinolyzed vinca alkaloids at the dosage of 1 mg/kg. Besides, The vinca alkaloid dipeptide derivatives groups did not lead to significantly body weight lose and organs damage. But the body weight of vinca alkaloids groups and hydrazinolyzed vinca alkaloids groups declined dramatically, and the damage of liver, spleen and other organs appeared.

TABLE 4

Inhibitory effects of vinca alkaloid derivatives on MDA-MB-231 xenografts in nude mice

| Compound | Dosage | Body weight (g) Pre-dose | Post-dose | Tumor weight (g) | Anti-tumor rate (%) |
|---|---|---|---|---|---|
| Saline | — | 20.3 ± 2.3 | 25.5 ± 3.6 | 2.61 ± 0.73 | — |
| VLB | 1 mg/kg | 20.7 ± 1.4 | 18.3 ± 2.4* | 1.22 ± 0.35 | 53.26** |
| JJ-CCJ | 1 mg/kg | 20.3 ± 0.7 | 16.4 ± 1.7* | 0.32 ± 0.03 | 87.74** |
| BX-CCJ | 1 mg/kg | 19.8 ± 1.0 | 21.2 ± 2.1 | 0.20 ± 0.12 | 92.34** |
| JJ-CCRB | 1 mg/kg | 21.0 ± 2.7 | 16.7 ± 1.4* | 0.59 ± 0.18 | 77.39** |
| BX-CCRB | 1 mg/kg | 19.1 ± 1.7 | 20.1 ± 0.9 | 0.37 ± 0.07 | 85.83** |
| JJ-CCFN | 1 mg/kg | 19.7 ± 2.1 | 16.3 ± 0.7* | 0.65 ± 0.13 | 75.10** |
| BX-CCFN | 1 mg/kg | 20.2 ± 0.7 | 20.6 ± 1.6 | 0.31 ± 0.11 | 88.13** |
| JJ-CCXJ | 1 mg/kg | 21.1 ± 2.5 | 17.3 ± 1.2* | 0.63 ± 0.15 | 75.86** |
| BX-CCXJ | 1 mg/kg | 19.5 ± 1.4 | 21.9 ± 2.9 | 0.23 ± 0.09 | 91.18** |

*P < 0.05,
**P < 0.01 vs control

TABLE 5

Inhibitory effects of vinca alkaloid derivatives on HepG2 xenografts in nude mice

| Compound | Dosage | Body weight (g) Pre-dose | Body weight (g) Post-dose | Tumor weight (g) | Anti-tumor rate (%) |
|---|---|---|---|---|---|
| Saline | — | 21.8 ± 1.0 | 27.3 ± 1.9 | 2.55 ± 0.68 | — |
| VLB | 1 mg/kg | 21.9 ± 0.7 | 18.2 ± 1.8* | 1.46 ± 0.27 | 42.75* |
| JJ-CCJ | 1 mg/kg | 21.7 ± 1.2 | 16.1 ± 0.3** | 0.57 ± 0.7 | 77.65** |
| BX-CCJ | 1 mg/kg | 22.0 ± 1.7 | 22.1 ± 1.3 | 0.34 ± 0.21 | 86.67** |
| JJ-CCRB | 1 mg/kg | 21.9 ± 1.6 | 17.0 ± 0.8* | 0.63 ± 0.29 | 75.29** |
| BX-CCRB | 1 mg/kg | 22.2 ± 1.5 | 22.6 ± 0.5 | 0.37 ± 0.09 | 85.49** |
| JJ-CCFN | 1 mg/kg | 22.3 ± 1.7 | 16.5 ± 0.4** | 0.62 ± 0.19 | 75.69** |
| BX-CCFN | 1 mg/kg | 21.9 ± 1.3 | 22.1 ± 1.2 | 0.30 ± 0.17 | 88.24** |
| JJ-CCXJ | 1 mg/kg | 22.0 ± 2.1 | 17.8 ± 0.9** | 0.53 ± 0.12 | 79.21** |
| BX-CCXJ | 1 mg/kg | 22.2 ± 1.2 | 21.9 ± 2.1 | 0.29 ± 0.13 | 88.63** |

*P < 0.05,
**P < 0.01 vs control

TABLE 6

Inhibitory effects of vinca alkaloid derivatives on LOVO xenografts in nude mice

| Compound | Dosage | Body weight (g) Pre-dose | Body weight (g) Post-dose | Tumor weight (g) | Anti-tumor rate (%) |
|---|---|---|---|---|---|
| Saline | — | 22.9 ± 0.9 | 26.2 ± 1.0 | 2.87 ± 0.47 | — |
| VLB | 1 mg/kg | 23.1 ± 1.4 | 19.6 ± 1.5* | 1.59 ± 0.51 | 44.60* |
| JJ-CCJ | 1 mg/kg | 22.8 ± 1.7 | 17.3 ± 1.2** | 0.64 ± 0.21 | 77.71** |
| BX-CCJ | 1 mg/kg | 23.8 ± 1.9 | 24.4 ± 1.6 | 0.43 ± 0.38 | 85.02** |
| JJ-CCRB | 1 mg/kg | 23.2 ± 2.1 | 16.4 ± 0.7** | 0.87 ± 0.16 | 69.69** |
| BX-CCRB | 1 mg/kg | 23.6 ± 1.2 | 24.1 ± 2.3 | 0.57 ± 0.23 | 80.14** |
| JJ-CCFN | 1 mg/kg | 22.7 ± 1.5 | 18.9 ± 2.1* | 0.68 ± 0.13 | 76.31** |
| BX-CCFN | 1 mg/kg | 23.6 ± 1.3 | 24.5 ± 1.5 | 0.47 ± 0.31 | 83.63** |
| JJ-CCXJ | 1 mg/kg | 22.9 ± 2.3 | 17.5 ± 1.3** | 0.76 ± 0.16 | 73.52** |
| BX-CCXJ | 1 mg/kg | 23.8 ± 1.0 | 24.2 ± 1.7 | 0.59 ± 0.33 | 79.45** |

*P < 0.05,
**P < 0.01 vs control

TABLE 7

Inhibitory effects of vinca alkaloid derivatives on K562 xenografts in nude mice

| Compound | Dosage | Body weight (g) Pre-dose | Body weight (g) Post-dose | Tumor weight (g) | Anti-tumor rate (%) |
|---|---|---|---|---|---|
| Saline | — | 21.8 ± 1.1 | 25.5 ± 1.7 | 1.68 ± 0.32 | — |
| VLB | 1 mg/kg | 21.9 ± 0.7 | 17.4 ± 0.4* | 0.86 ± 0.10 | 49.81* |
| JJ-CCJ | 1 mg/kg | 22.1 ± 1.9 | 16.5 ± 0.8** | 0.53 ± 0.19 | 68.45** |
| BX-CCJ | 1 mg/kg | 22.3 ± 1.0 | 23.1 ± 1.4 | 0.39 ± 0.27 | 76.79** |
| JJ-CCRB | 1 mg/kg | 21.8 ± 1.4 | 18.2 ± 0.5* | 0.68 ± 0.20 | 59.52** |
| BX-CCRB | 1 mg/kg | 22.1 ± 0.5 | 23.4 ± 1.2 | 0.46 ± 0.29 | 72.62** |
| JJ-CCFN | 1 mg/kg | 21.5 ± 2.1 | 17.4 ± 0.9* | 0.71 ± 0.21 | 57.74** |
| BX-CCFN | 1 mg/kg | 22.9 ± 1.3 | 23.0 ± 0.8 | 0.57 ± 0.13 | 66.08** |
| JJ-CCXJ | 1 mg/kg | 22.4 ± 1.7 | 17.1 ± 0.3** | 0.67 ± 0.22 | 60.12** |
| BX-CCXJ | 1 mg/kg | 21.2 ± 0.9 | 22.5 ± 1.1 | 0.42 ± 0.14 | 75.00** |

*P < 0.05,
**P < 0.01 vs control

TABLE 8

Inhibitory effects of vinca alkaloid derivatives on HL-60 xenografts in nude mice

| Compound | Dosage | Body weight (g) Pre-dose | Body weight (g) Post-dose | Tumor weight (g) | Anti-tumor rate (%) |
|---|---|---|---|---|---|
| Saline | — | 19.9 ± 1.8 | 22.7 ± 1.6 | 2.08 ± 0.38 | — |
| VLB | 1 mg/kg | 19.4 ± 1.0 | 16.2 ± 0.7* | 0.98 ± 0.25 | 52.89** |
| JJ-CCJ | 1 mg/kg | 20.1 ± 1.7 | 16.1 ± 0.4* | 0.64 ± 0.17 | 69.23** |
| BX-CCJ | 1 mg/kg | 18.8 ± 1.1 | 20.1 ± 1.0 | 0.41 ± 0.19 | 81.29** |
| JJ-CCRB | 1 mg/kg | 19.5 ± 1.3 | 17.1 ± 0.3* | 0.72 ± 0.21 | 65.38** |
| BX-CCRB | 1 mg/kg | 19.0 ± 1.2 | 19.2 ± 1.3 | 0.53 ± 0.28 | 74.52** |
| JJ-CCFN | 1 mg/kg | 19.2 ± 1.9 | 17.3 ± 0.1* | 0.83 ± 0.13 | 60.10** |
| BX-CCFN | 1 mg/kg | 18.7 ± 1.4 | 18.6 ± 1.4 | 0.61 ± 0.35 | 70.68** |
| JJ-CCXJ | 1 mg/kg | 19.7 ± 1.5 | 16.3 ± 0.6* | 0.84 ± 0.13 | 59.62** |
| BX-CCXJ | 1 mg/kg | 19.3 ± 1.1 | 19.7 ± 0.9 | 0.58 ± 0.17 | 72.12** |

*P < 0.05,
**P < 0.01 vs control

Figure 3:
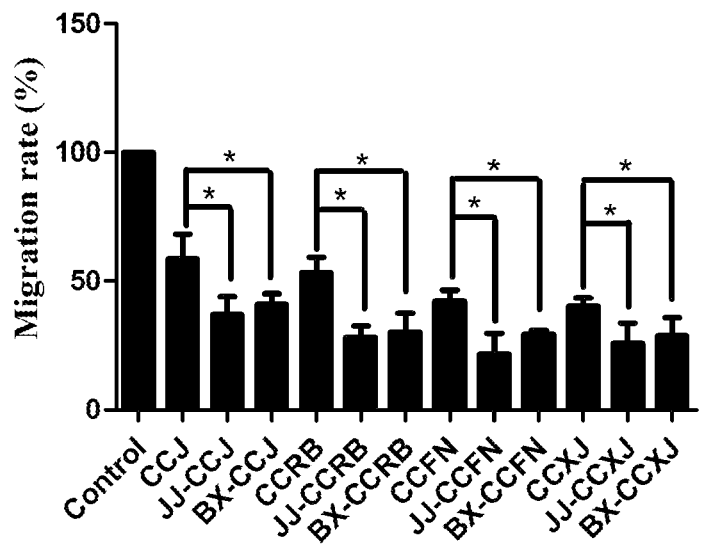

Example 8. Inhibitory Effects of Vinca Alkaloid Derivatives on the Invasion Capacity of HUVECs Experimental method: The HUVECs at logarithmic phase were digested, centrifuged and counted. Then, cells ($5 \times 10^6$/mL) were added to the transwell system coated with Matrigel (BD Bioscience), with each well 0.1 mL. After 24 h of incubation at 37° C. with 5% $CO_2$, blank control group and drug groups were set up, the drug groups were added vinca alkaloids and vinca alkaloid derivatives respectively. Final concentration of drugs was 100 pmol/L. After 24 h, medium was removed and cells were washed with PBS, fixed with 4% (W/V) paraformaldehyde for 15 min and stained with Giemsa Stain for 30 min, followed by once washed with PBS. Images were recorded and cell numbers were counted. The results were shown in FIG. 3.

Results showed that vinca alkaloids, hydrazinolyzed vinca alkaloids and vinca alkaloid dipeptide derivatives all inhibited the invasion of HUVECs. Besides, compared with vinca alkaloids, hydrazinolyzed vinca alkaloids and vinca alkaloid dipeptide derivatives more significantly suppressed the invasion of HUVECs.

Figure 4:
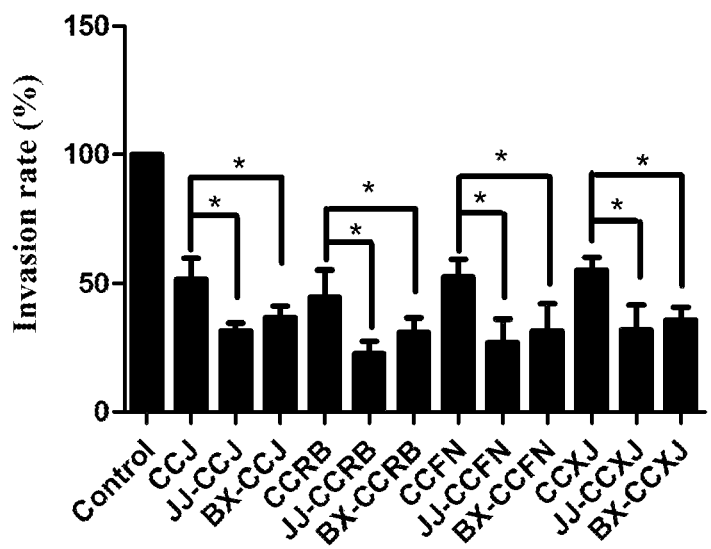

Example 9. Inhibitory Effects of Vinca Alkaloid Derivatives on Migration Capacity of HUVECs Experimental method: The HUVECs at logarithmic phase were centrifuged and resuspended in serum-free medium after being washed with PBS. Then, cells ($2 \times 10^6$/mL) were added to the transwell system, with each well 100 µL. Blank control group and drug groups were set up, the drug groups were added with vinca alkaloid Vinblastine (CCJ), Vinorelbine (CCRB), Vinflunine (CCFN), Vincristine (CCXJ) and vinca alkaloid derivatives hydrazinolyzed Vinblastine (JJ-CCJ), Vinblastine dipeptide (BX-CCJ), hydrazinolyzed Vinorelbine (JJ-CCRB), Vinorelbine dipeptide (BX-CCRB), hydrazinolyzed Vinflunine (JJ-CCFN), Vinflunine dipeptide (BX-CCFN), hydrazinolyzed Vincristine (JJ-CCXJ), Vincristine dipeptide (BX-CCXJ) respectively. Final concentration of drugs was 100 pmol/L. 700 µL RPMI-1640 medium containing 10% new bovine serum was added to the lower chamber. After 24 h of incubation at 37° C. with 5% $CO_2$, the medium was removed and the cells were fixed with 4% paraformaldehyde for 30 min at 4° C., washed with water slowly twice and stained with Giemsa Stain for 30 min Afterward, cells on the surface of the membrane were gently scraped away with cotton swabs. The remaining cells were washed with water slowly. Images were recorded and cell numbers were counted. The results were shown in FIG. 4.

Results: Compared with vinca alkaloids, vinca alkaloid derivatives which obtained from Example 1 significantly suppressed the migration of HUVECs. Results showed that vinca alkaloids, hydrazinolyzed vinca alkaloids and vinca alkaloid dipeptide derivatives all inhibited the migration of HUVECs. What's more, compared with vinca alkaloids, hydrazinolyzed vinca alkaloids and vinca alkaloid dipeptide derivatives suppressed the migration of HUVECs more significantly.

Figure 5:
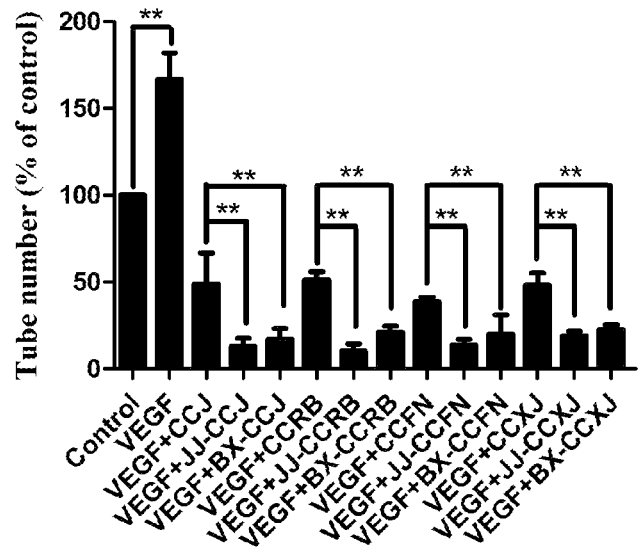

Example 10. Inhibitory Effects of Vinca Alkaloid Derivatives on Tube Formation of HUVECs Experimental method: Matrigel was added into a pre-cooled 48 well plates, with each well 100 μL, and then incubated at 37° C. for 20 min. After the Matrigel solidified, $1 \times 10^5$ cells/well were seeded onto the Matrigel, and the medium were pre-added with vinca alkaloids, vinca alkaloid derivatives JJ-CCJ, BX-CCJ, JJ-CCRB, BX-CCRB, JJ-CCFN, BX-CCFN, JJ-CCXJ, BX-CCXJ (final concentration 100 pmol/L) and VEGF (final concentration 100 ng/mL). The well without drugs and VEGF was taken as blank control. After 8 h of incubation, the formation of tubuelar structures were observed and photographed under inverted microscope. The results were shown in FIG. 5.

Results showed that vinca alkaloids, hydrazinolyzed vinca alkaloids and vinca alkaloid dipeptide derivatives all inhibited the VEGF-mediated tube formation of HUVECs. Besides, compared with vinca alkaloids, hydrazinolyzed vinca alkaloids and vinca alkaloid dipeptide derivatives more significantly suppressed the tube formation of HUVECs.

Figure 6:
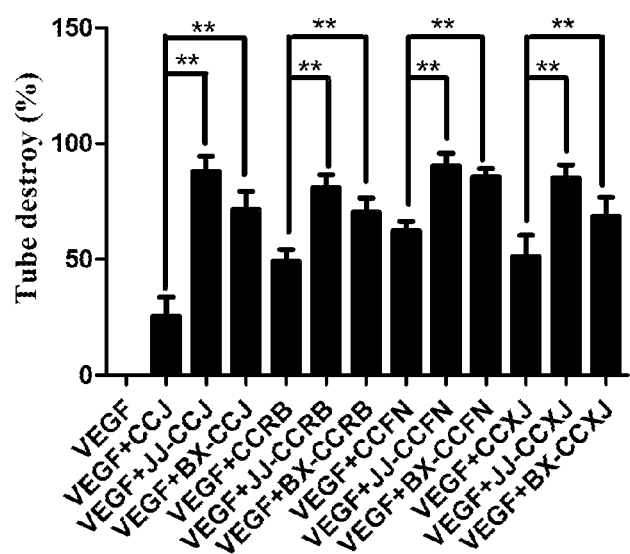

Example 11. Disruptive Effects of Vinca Alkaloid Derivatives on Preformed Tubular Structures of HUVECs Experimental method: According to the literature [Zhi-Ting Deng, et al. *Biochemical Pharmacology* 2011, 82:1832-42], and to optimize. Matrigel was added into a pre-cooled 48 well plates, with each well 100 μL, and then incubated at 37° C. for 20 min After the Matrigel solidified, $1 \times 10^5$ cells/well were seeded onto the Matrigel and incubated 4 h. When the tubuelar structures formed, the medium was changed with which containing vinca alkaloids, vinca alkaloid derivatives JJ-CCJ, BX-CCJ, JJ-CCRB, BX-CCRB, JJ-CCFN, BX-CCFN, JJ-CCXJ, BX-CCXJ (final concentration 100 pmol/L) and VEGF (final concentration 100 ng/mL) respectively. The well without drugs and VEGF was taken as blank control. After 8 h of incubation, the formation of tubuelar structures were observed and photographed under inverted microscope. The results were shown in FIG. 6.

Results showed that vinca alkaloids, hydrazinolyzed vinca alkaloids and vinca alkaloid dipeptide derivatives all destroyed the preformed tubuelar structures of HUVECs induced by VEGF. What's more, compared with vinca alkaloids, the hydrazinolyzed vinca alkaloids and vinca alkaloid dipeptide derivatives more significantly destroyed the preformed tubuelar structures of HUVECs induced by VEGF.

Example 12. Inhibitory Effects of Vinca Alkaloid Derivatives on Vessel Growth of Chick Embryo Chorioallantoic Membrane (CAM)

Figure 7:
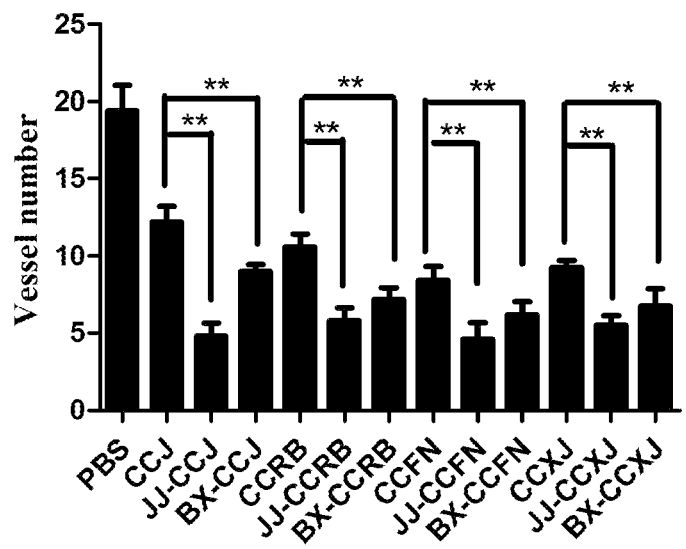

Experimental method: According to the literature [Cho S G, et al. *Cancer Res.* 2009, 69(17): 7062-7070], 60 five-day-old embryonic eggs were divided randomly into PBS group, vinca alkaloids group, vinca alkaloid derivatives JJ-CCJ group, BX-CCJ group, JJ-CCRB group, BX-CCRB group, JJ-CCFN group, BX-CCFN group, JJ-CCXJ group and BX-CCXJ group, with 10 eggs in each group. Embryonic eggs were placed in 37° C. incubator after sterilizing with the air chamber up. After 8 days of incubation, a 1.5 cm×1.5 cm window was opened at the air chamber of the eggs and the shell membrane was removed to expose the CAM. Then, filter paper with drugs were placed on the chick chorioallantoic membrane (CAM) where vessels are less. The window was sealed and the eggs were returned to the incubator. After further incubation for one day, remove the sealing membrane. The chick chorioallantoic membrane (CAM) was fixed with methanol:acetone (1:1, V/V) for 15 min at room temperature. After the vessels were solidified, the membrane was cut by centering around the filter paper, and transferred to culture dish, which contained a small amount of water, then unfolded over the filter paper. After that, the filter paper, along with the membrane, was taken out from the water. Vessels within the scope of 5 mm of experimental part edge was observed, counted and photographed. The results were shown in FIG. 7.

Results showed that vinca alkaloids, hydrazinolyzed vinca alkaloids and vinca alkaloid dipeptide derivatives all inhibited the vessel growth of CAM. Moreover, compared with vinca alkaloids, hydrazinolyzed vinca alkaloids and vinca alkaloid dipeptide derivatives more significantly suppressed the vessel growth of CAM.

Example 13. Disruptive Effects of Vinca Alkaloid Derivatives on Preformed Vessel of Chick Embryo Chorioallantoic Membrane (CAM)

Figure 8:
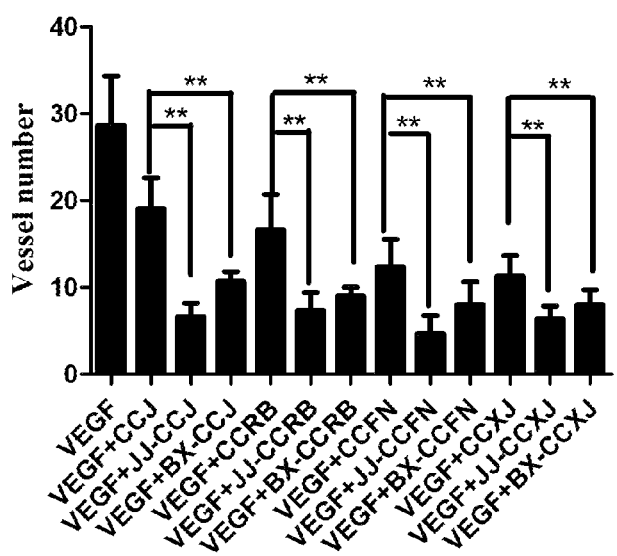
FIG. 8. Disruptive effects of vinca alkaloid derivatives on preformed vessel of chick embryo chorioallantoic membrane (CAM)

Experimental method: 60 five-day-old embryonic eggs were divided randomly into vinca alkaloids group, vinca alkaloid derivatives JJ-CCJ group, BX-CCJ group, JJ-CCRB group, BX-CCRB group, JJ-CCFN group, BX-CCFN group, JJ-CCXJ group and BX-CCXJ group, with 10 eggs in each group. Embryonic eggs were placed in 37° C. incubator after sterilizing with the air chamber up. After 8 days of incubation, a 1.5 cm×1.5 cm window was opened at the air chamber of the eggs and the shell membrane was removed to expose the CAM. Then, a filter paper with VEGF (100 nmol) were placed on the CAM where vessels are less. The window was sealed and the eggs were returned to the incubator. After incubating for another one day, remove the sealing membrane. Vinca alkaloids, vinca alkaloid derivatives JJ-CCJ, BX-CCJ, JJ-CCRB, BX-CCRB, JJ-CCFN, BX-CCFN, JJ-CCXJ and BX-CCXJ (1 nmol for each) were added onto the filter papers respectively. Then the window was sealed again. After further incubation for one day, the sealing film was removed. The CAM was fixed with methanol:acetone (1:1, V/V) for 15 min at room temperature. After the vessels were solidified, the membrane was cut by centering around the filter paper, and transferred to culture dish, which contained a small amount of water, then unfolded over the filter paper. Afterward, the filter paper, along with the membrane, was taken out from the water. Vessels within the scope of 5 mm of experimental part edge was observed, counted and photographed. The results were shown in FIG. 8.

Results showed that vinca alkaloids, hydrazinolyzed vinca alkaloids and vinca alkaloid dipeptide derivatives all destroyed preformed vessel of CAM. What's more, compared with vinca alkaloids, the hydrazinolyzed vinca alkaloids and vinca alkaloid dipeptide derivatives more significantly destroyed the preformed vessel of CAM.

Figure 9:
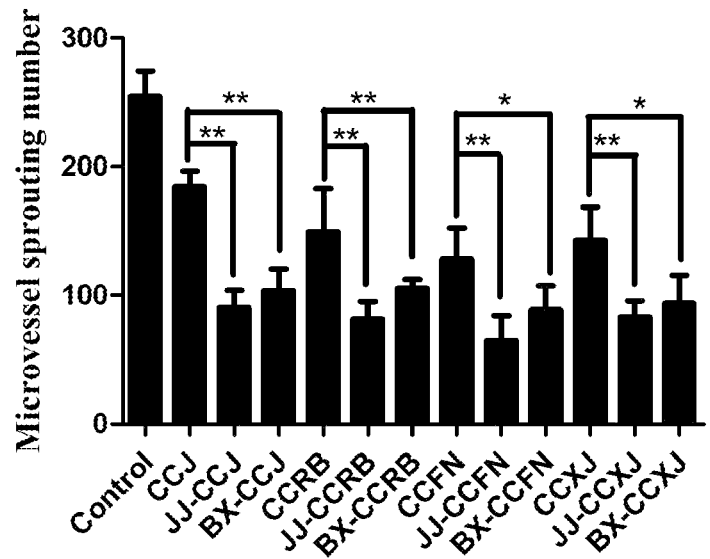
FIG. 9. Inhibitory effects of vinca alkaloid derivatives on microvessel growth of rat aortic ring FIG. 10. Disruptive effects of vinca alkaloid derivatives on preformed microvessel of rat aortic ring FIG. 11. Inhibitory effects of vinca alkaloid derivatives on vessel growth of matrigel plug FIG. 12. Disruptive effects of vinca alkaloid derivatives on preformed vessel of matrigel plug FIG. 13. Inhibitory effects of vinca alkaloid derivatives on vessel growth of rat corneal micropocket FIG. 14. Disruptive effects of vinca alkaloid derivatives on preformed vessel of rat corneal micropocket FIG. 15. Inhibitory effects of vinca alkaloid derivatives on the angiogenesis in synovial tissue of CIA mouse FIG. 16. Disruptive effects of vinca alkaloid derivatives on preformed vessel in synovial tissue of CIA mouse In FIGS. 3-16, *refers to $P<0.05$, **refers to $P<0.01$

Example 14. Inhibitory Effects of Vinca Alkaloid Derivatives on Microvessel Growth of Rat Aortic Ring Experimental method: According to the literature method [Srinivas Reddy Boreddy, et al. *PLoS One*. 2011, 6(10): e25799], 100 µL pre-cooled and well-dissolved Matrigel was added into the pre-cooled 48 well plates and then incubated at 37° C. for 30 min until the Matrigel solidified. During this period, Sprague Dawley rat was put into the 75% alcohol for 3 min after $CO_2$ euthanasia. Then split the mouse thorax on bacteria-free operating bench and separated the thoracic aorta. After washing with PBS, the aortas isolated from rat were transferred to DMEM/F12 complete medium, cleaned off connective tissues and periadventitial fat, and then cut it into 1 mm long rings with ophthalmic scissors. The rings were placed on the Matrigel and covered with an additional 100 µL of pre-cooled Matrigel. After 30 min of incubation at 37° C., blank control group and drug groups were set up, the drug groups were added with DMEM-F12 complete medium containing 2 nmol/L vinca alkaloids and vinca alkaloid derivatives JJ-CCJ, BX-CCJ, JJ-CCRB, BX-CCRB, JJ-CCFN, BX-CCFN, JJ-CCXJ, BX-CCXJ (containing 100 ng/mL VEGF) respectively. The medium was replaced every two days, after the fourth replacement, the microvessel growth was photographed under inverted microscope and quantified. The results were shown in FIG. 9.

Results showed that vinca alkaloids, hydrazinolyzed vinca alkaloids and vinca alkaloid dipeptide derivatives all inhibited the microvessel growth of rat aortic ring. Besides, compared with vinca alkaloids, the hydrazinolyzed vinca alkaloids and vinca alkaloid dipeptide derivatives more significantly inhibited the microvessel growth of rat aortic ring.

Figure 10:
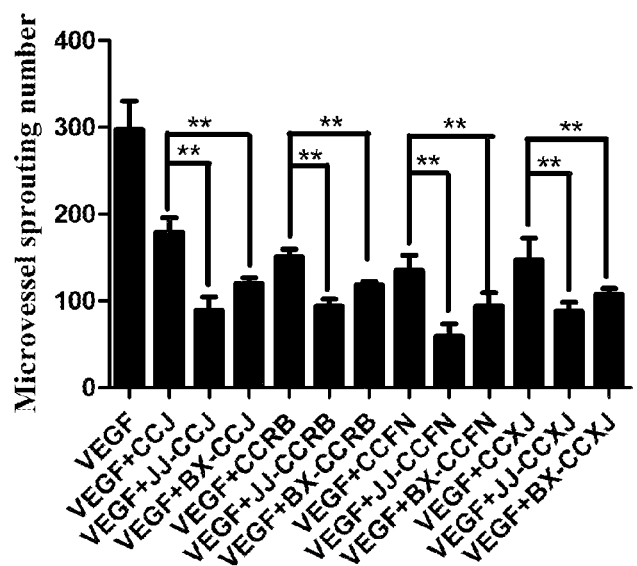

Example 15. Disruptive Effects of Vinca Alkaloid Derivatives on Preformed Microvessel of Rat Aortic Ring Experimental method: According to the literature [Deng Z T, et al. *Biochemical Pharmacology* 2011, 82:1832-42], and to optimize. 100 µL pre-cooled and well dissolved Matrigel was added to the pre-cooled 48 well plates and then incubated at 37° C. for 30 min until the Matrigel solidified. During this period, SD rat was put into the 75% alcohol for 3 min after $CO_2$ euthanasia. Then split the mouse thorax on bacteria-free operating bench and separated the thoracic aorta. After washing with PBS, the aortas isolated from rat were transferred to complete DMEM/F12 medium, cleaned off connective tissues and periadventitial fat with scissors and tweezers, and then cut it into 1 mm long rings with ophthalmic scissors. The rings were placed on the Matrigel and covered with an additional 100 µL of pre-cooled Matrigel. After 30 min of incubation at 37° C., complete DMEM-F12 medium were added (containing 100 ng/mL VEGF). The medium was replaced every two days, when the microvessel formed, DMEM-F12 complete medium containing 2 nmol/L vinca alkaloids and vinca alkaloid derivatives JJ-CCJ, BX-CCJ, JJ-CCRB, BX-CCRB, JJ-CCFN, BX-CCFN, JJ-CCXJ and BX-CCXJ were added respectively. 24 h later, the microvessel growth was photographed under inverted microscope and quantified by manual counting. The results were shown in FIG. 10.

Results showed that vinca alkaloids, hydrazinolyzed vinca alkaloids and vinca alkaloid dipeptide derivatives all destroyed the preformed microvessel of rat aortic ring. What's more, compared with vinca alkaloids, the hydrazinolyzed vinca alkaloids and vinca alkaloid dipeptide derivatives more significantly destroyed the preformed microvessel of rat aortic ring.

Figure 11:
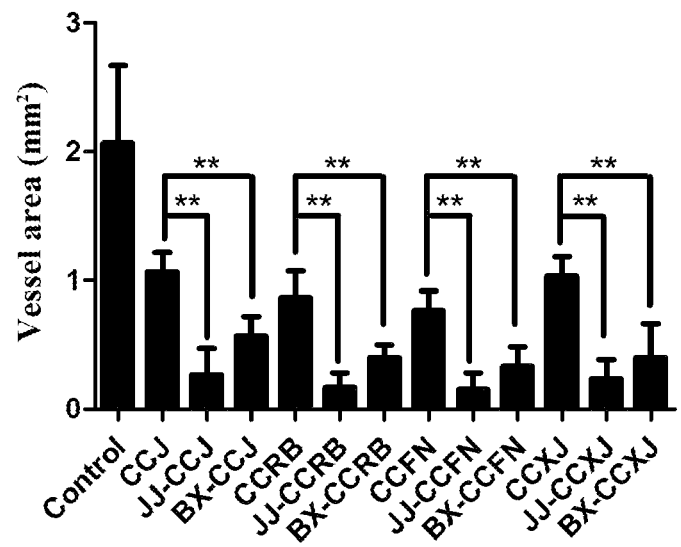

Example 16. Inhibitory Effects of Vinca Alkaloid Derivatives on Vessel Growth of Matrigel Plug Experimental method: According to the literature method [Nasim Akhtar, et al. *Angiogenesis*. 2002, 5: 75-80], 500 µL, pre-cooled Matrigel:PBS (1:1, V/V) was mixed with 500 ng VEGF and 150 units heparin, and then mixed with vinca alkaloids and vinca alkaloid derivatives JJ-CCJ, BX-CCJ, JJ-CCRB, BX-CCRB, JJ-CCFN, BX-CCFN, JJ-CCXJ, BX-CCXJ (final concentration of drugs was 100 pmol/L) respectively. The Matrigel mixture was injected subcutaneously into the back of 6-week-old BALB/C nu/nu mice. The PBS group was taken as blank control, each group of 6 mice. The mice were euthanasiaed with $CO_2$ at 14 days, the Matrigel plugs were removed and fixed in 4% paraformaldehyde for 24 h, then embedded in paraffin and stained with hematoxylin and eosin (H&E). The vessel growth was observed, photographed and counted under inverted microscope. The results were shown in FIG. 11.

Results showed that vinca alkaloids, hydrazinolyzed vinca alkaloids and vinca alkaloid dipeptide derivatives all inhibited the vessel growth of Matrigel Plug. Besides, compared with vinca alkaloids, the hydrazinolyzed vinca alkaloids and vinca alkaloid dipeptide derivatives more significantly inhibited the vessel growth of Matrigel Plug.

Figure 12:
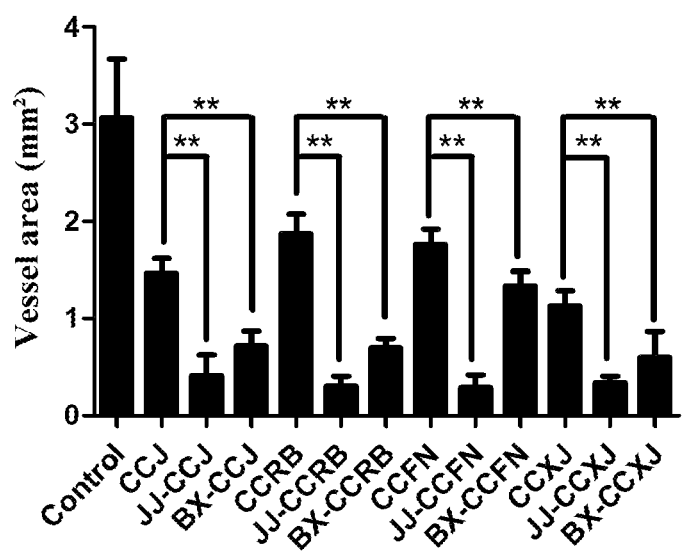

Example 17. Disruptive Effects of Vinca Alkaloid Derivatives on Preformed Vessel of Matrigel Plug Experimental method: According to the literature method Nasim Akhtar, et al. *Angiogenesis*. 2002, 5: 75-801, and to optimize. 500 µL pre-cooled Matrigel was mixed with 500 ng VEGF and 150 units heparin and then injected subcutaneously into the back of 6-week-old BALB/C nu/nu mice. One week later, the mice were intravenously (i.v.) injected every two days with 1 mg/kg of vinca alkaloids and vinca alkaloid derivatives JJ-CCJ, BX-CCJ, JJ-CCRB, BX-CCRB, JJ-CCFN, BX-CCFN, JJ-CCXJ, BX-CCXJ. The saline group was taken as blank control, each group of 6 mice. The mice were practiced for $CO_2$ euthanasia after 7 injection, the matrigel plugs were removed and fixed in 4% paraformaldehyde for 24 h, then embedded in paraffin and stained with H&E. The vessel growth was observed, photographed and counted under inverted microscope. The results were shown in FIG. 12.

Results showed that vinca alkaloids, hydrazinolyzed vinca alkaloids and vinca alkaloid dipeptide derivatives all destroyed the preformed vessel of Matrigel Plug. What's more, compared with vinca alkaloids, the hydrazinolyzed vinca alkaloids and vinca alkaloid dipeptide derivatives more significantly destroy the preformed vessel of Matrigel Plug.

Figure 13:
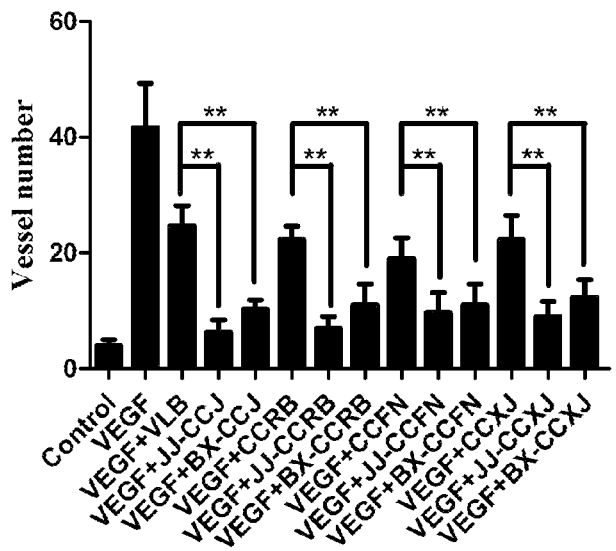

Example 18. Inhibitory Effects of Vinca Alkaloid Derivatives on Vessel Growth of Rat Corneal Micropocket Experimental method: Rat corneal micropocket model was established according to the literature method [Yi Z F, et al. *Int J Cancer.* 2009, 124: 843-852]. Briefly, the slow-release pellet containing 200 ng VEGF was made of ulcerlmin and Poly-HEMA. Following anesthesia with an injection of 2% Nembutal, VEGF pellets were implanted into rat corneal micropocket. The cornea was covered with Chloramphenicol hydrochloride after surgery. On the day after operation, rats were divided randomly into PBS group, vinca alkaloids group, vinca alkaloid derivatives JJ-CCJ group, BX-CCJ group, JJ-CCRB group, BX-CCRB group, JJ-CCFN group, BX-CCFN group, JJ-CCXJ group and BX-CCXJ group, with 10 rats in each group. The mice were intravenously (i.v.) injected every two days with these drug at the dose of 1 mg/kg. Both the vascular length (VL) and clocks of neoneovascularization (CN) were observed and recorded after 7th injection. The formula below was used to determine the neoneovascularization area: Area $(mm^2)=0.2\times \pi \times VL$ (mm)$\times CN$ (mm) The results were shown in FIG. 13.

Results showed that vinca alkaloids, hydrazinolyzed vinca alkaloids and vinca alkaloid dipeptide derivatives all inhibited the vessel growth of rat corneal micropocket. Besides, compared with vinca alkaloids, the hydrazinolyzed vinca alkaloids and vinca alkaloid dipeptide derivatives more significantly inhibited the vessel growth of rat corneal micropocket.

Figure 14:
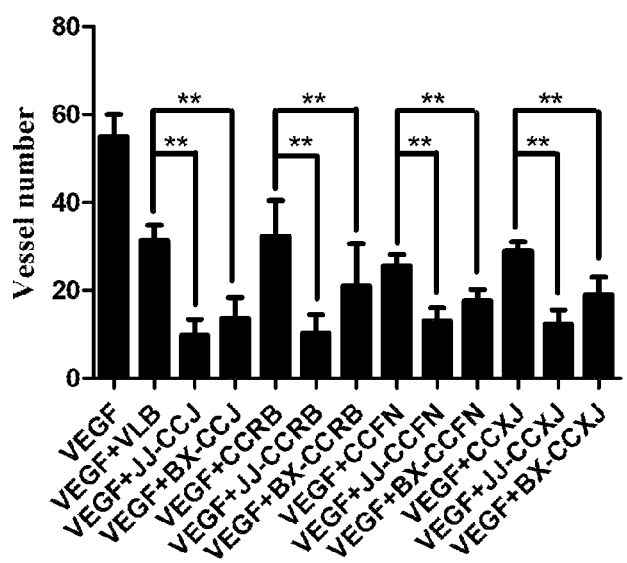

Example 19. Disruptive Effects of Vinca Alkaloid Derivatives on Preformed Vessel of Rat Corneal Micropocket Experimental method: Rat corneal micropocket model was established according to the method from literature [Yi Z F, et al. *Int J Cancer.* 2009, 124: 843-852], and to optimize. Briefly, the slow-release pellet containing 200 ng VEGF was made of ulcerlmin and Poly-HEMA. Following anesthesia with an injection of 2% Nembutal, VEGF pellets were implanted into rat corneal micropocket. The cornea was covered with Chloramphenicol hydrochloride after surgery. On the day after operation, rats were divided randomly into PBS group, vinca alkaloids group, vinca alkaloid derivatives JJ-CCJ group, BX-CCJ group, JJ-CCRB group, BX-CCRB group, JJ-CCFN group, BX-CCFN group, JJ-CCXJ group and BX-CCXJ group, with 10 rats in each group. One week later when small vessels were formed, 1 mg/kg drugs were given respectively every two days by intravenous injection for 7th. Both the length and clocks of neoneovascularization were observed and recorded. The formula below was used to determine the neoneovascularization area: Area $(mm^2)=0.2\times \pi \times VL$ (mm)$\times CN$ (mm) The results were shown in FIG. 14.

Results showed that vinca alkaloids, hydrazinolyzed vinca alkaloids and vinca alkaloid dipeptide derivatives all destroyed the preformed vessel of rat corneal micropocket. What's more, compared with vinca alkaloids, the hydrazinolyzed vinca alkaloids and vinca alkaloid dipeptide derivatives more significantly destroyed the preformed vessel of rat corneal micropocket.

Figure 15:
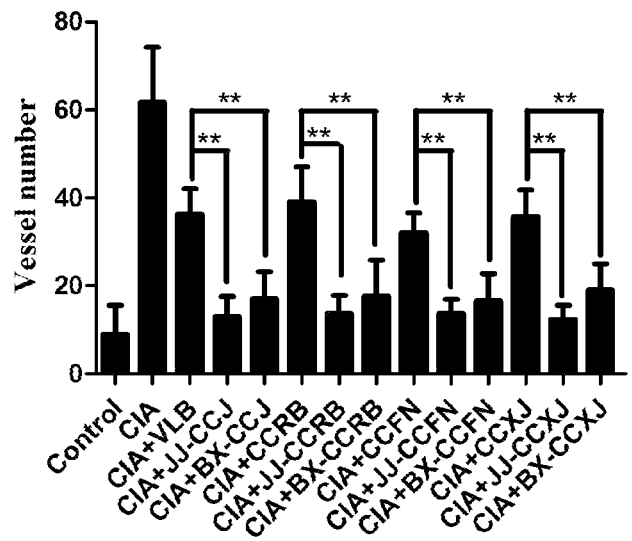

Example 20. Inhibitory Effects of Vinca Alkaloid Derivatives on the Angiogenesis in Synovial Tissue of CIA Mouse Experimental method: CIA model (antigen-induced arthritis) in C57 mouse was established according to the method from literature [Campbell I K, et al. Eur J Immunol, 2000, 30: 1568-1575]. Each mouse was injected i.d. at several sites into the base of the tail with 100 µL emulsion consisting 100 µg type II collagen. Mouse injected i.d. with saline was taken as control group and with the same method as model groups. Mice were divided randomly, with 10 mice in each group. On day one after molding, PBS, vinca alkaloids, vinca alkaloid derivatives JJ-CCJ, BX-CCJ, JJ-CCRB, BX-CCRB, JJ-CCFN, BX-CCFN, JJ-CCXJ and BX-CCXJ (1.0 mg/kg) were administered every other day by tail vein injection respectively. Briefly, mice were killed by $CO_2$ asphyxiation after consecutive 7 administration. Then, joints were removed, trimmed of the surrounding musculature, and fixed with 4% paraformaldehyde for 24 h. The synovial tissue angiogenesis was tested according to immunohistochemical assay [Yajuan Song, et al. *Angiogenesis.* 2012, 15: 421-432], with CD31 as marker. The standard to assess microvessel was according to literature [Tatsuta M, et al. *Int J Cancer,* 1999, 80: 396-399]: brown dying single vascular cells or cell clusters were counted as one vessel. Large vessels with lumen greater than size of eight red blood cells or with thick muscular were not counted. Slices were examined under low power (×10) to select three regions of highest vessel density, then microvessels density (MVD) were counted in a ×40 field in each of these three regions. The results were shown in FIG. 15.

Results showed that vinca alkaloids, hydrazinolyzed vinca alkaloids and vinca alkaloid dipeptide derivatives all inhibited the angiogenesis in synovial tissue of CIA mouse. Besides, compared with vinca alkaloids, the hydrazinolyzed vinca alkaloids and vinca alkaloid dipeptide derivatives more significantly inhibited the angiogenesis in synovial tissue of CIA mouse.

Figure 16:
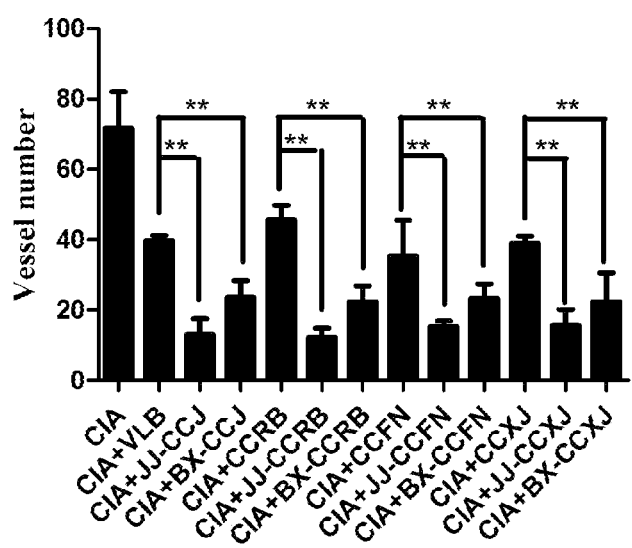

Example 21. Disruptive Effects of Vinca Alkaloid Derivatives on Preformed Vessel in Synovial Tissue of CIA Mouse Experimental method: CIA model in C57 mouse was established according to the method from literature [Campbell I K, et al. Eur J Immunol, 2000, 30: 1568-1575], and to optimize. Each mouse was injected i.d. at several sites into the base of the tail with 100 µL emulsion consisting 100 µg type II collagen. Mouse injected i.d. with saline was taken as control group and followed the method of the model group. Mice were divided randomly, with 10 mice in each group. After 7 days, PBS, vinca alkaloids, vinca alkaloid derivatives JJ-CCJ, BX-CCJ, JJ-CCRB, BX-CCRB, JJ-CCFN, BX-CCFN, JJ-CCXJ and BX-CCXJ (1.0 mg/kg) were intravenously (i.v.) injected every two days. Briefly, mice were killed by $CO_2$ asphyxiation after a total of 7 administration. Then, joints were removed, trimmed of the surrounding musculature, and fixed with 4% paraformaldehyde for 24 h. The synovial tissue angiogenesis was tested according to immunohistochemical assay [Yajuan Song, et al. *Angiogenesis.* 2012, 15: 421-432], with CD31 as marker. The standard to assess microvessel according to the literature [Tatsuta M, et al. *Int J Cancer,* 1999, 80: 396-399]: brown dying single vascular cells or cell clusters were counted as one vessel. Large vessels with lumen greater than size of eight red blood cells or with thick muscular were not counted. Slices were examined under low power (×10) to select three regions of highest vessel density, then microvessels density (MVD) were counted in a ×40 field in each of these three regions. The results were shown in FIG. 16.

Results showed that vinca alkaloids, hydrazinolyzed vinca alkaloids and vinca alkaloid dipeptide derivatives all destroyed the preformed vessel in synovial tissue of CIA mouse. What's more, compared with vinca alkaloids, the hydrazinolyzed vinca alkaloids and vinca alkaloid dipeptide derivatives more significantly destroyed the preformed vessel in synovial tissue of CIA mouse.

The above mentioned experimental results have confirmed that the vinca alkaloid derivatives of the invention can be applied in the treatment and prevention of the diseases, such as malignant tumor, diabetic retinopathy, rheumatoid arthritis, etc., in vivo and in vitro, particularly, the hydrazinolyzed vinca alkaloids and the vinca alkaloid dipeptide derivatives have better effects on preventing or treating the diseases, such as malignant tumor, diabetic retinopathy, rheumatoid arthritis, etc.

The above mentioned embodiments are the preferred embodiments of the present invention, but the embodiments of the present invention are not limited thereto, any other changes, modifications, substitutions, combinations, and simplifications made without departing from the spirit and principle of the present invention, which shall be the equivalent replacements, are all included within the scope of the present invention.

The invention claimed is:

1. A method for treating a disease in a subject comprising: administering to a subject a composition comprising a vinca alkaloid dipeptide derivative or a physiologically acceptable salt thereof, wherein the vinca alkaloid dipeptide derivative is selected from the group consisting of BX-CCXJ, BX-CCJ, BX-CCRB and BX-CCFN shown as follows

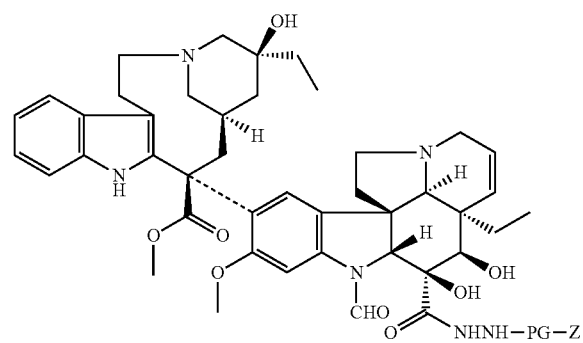
BX-CCXJ

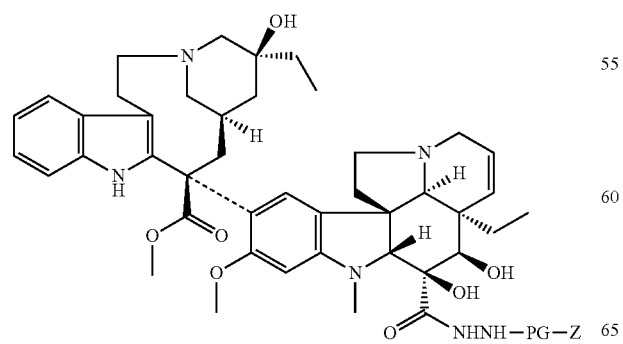
BX-CCJ

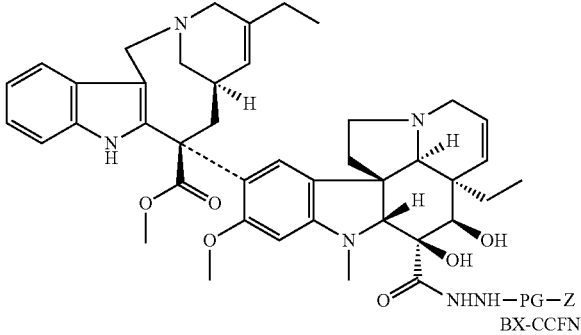
BX-CCRB

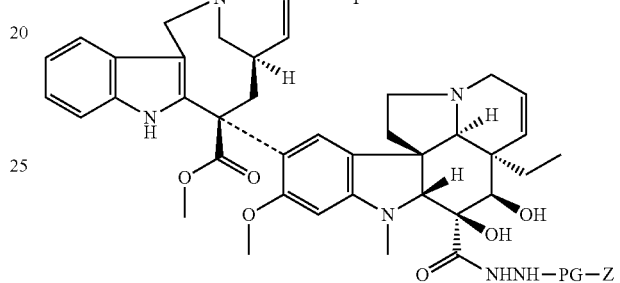
BX-CCFN wherein, -PG-Z represents a benzyloxycarbonylglycylprolyl group having the structure as follows

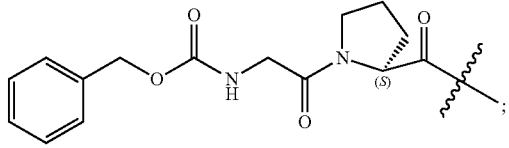

wherein the disease is a cancer selected from the group consisting of Hodgkin's lymphoma, non-Hodgkin's lymphoma, acute lymphoblastic leukemia, testicular cancer, non-small cell lung cancer, stomach cancer, nasopharyngeal cancer, breast cancer, intestinal cancer, liver cancer, leukemia, prostate cancer, cervical cancer, melanoma, ovarian cancer, neuroblastoma, nephroblastoma, rheumatoid arthritis, and diabetic retinopathy.

2. The method of claim 1, wherein the physiologically acceptable salt is selected from the group consisting of hydrochloride, sulfate, acetate, tartrate and citrate.

3. A method for preparing the vinca alkaloid dipeptide derivative of claim 1 or a pharmaceutically acceptable salt thereof, comprising the steps of:
(1) reacting a vinca alkaloid or a physiologically acceptable salt thereof with hydrazinolyzed hydrate to obtain a hydrazinolyzed vinca alkaloid;
(2) reacting the hydrazinolyzed vinca alkaloid with benzyloxycarbonylglycyl-proline under a condensing agent to obtain a vinca alkaloid dipeptide derivative;
wherein the hydrazinolyzed vinca alkaloid is selected from JJ-CCXJ or JJ-CCJ shown as follows

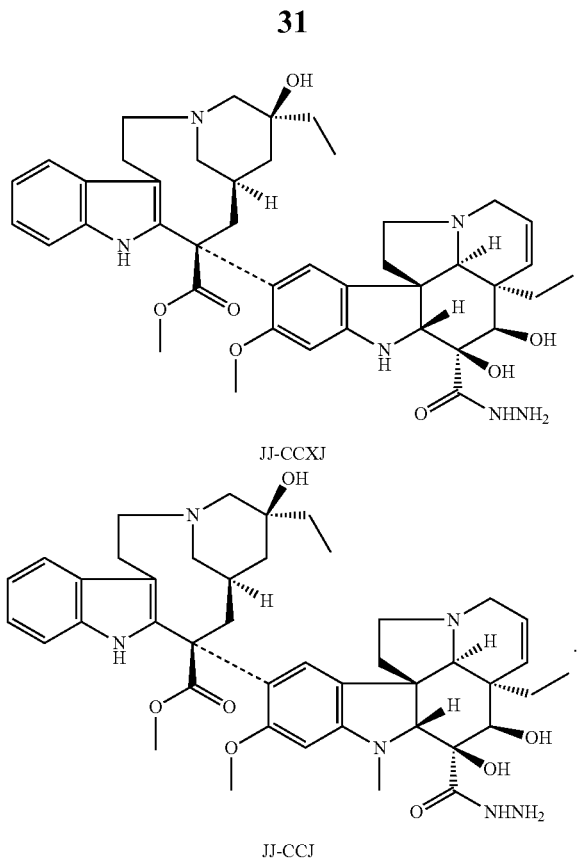

JJ-CCXJ

JJ-CCJ

4. The method according to claim 3, wherein the condensing agent is selected from the group consisting of ethyl chloroformate, 1-ethyl-(3-dimethylaminopropyl) carbodiimide hydrochloride, N,N'-diisopropyl carbodiimide, benzotriazol-1-yl-oxytripyrrolidino-phosphonium hexafluorophosphate and 1-chloro-N,N',2-trimethylacrylamide and any combination of ethyl chloroformate, 1-ethyl-(3-dimethylaminopropyl) carbodiimide hydrochloride, N,N'-diisopropyl carbodiimide, benzotriazol-1-yl-oxytripyrrolidino-phosphonium hexafluorophosphate and 1-chloro-N,N',2-trimethylacrylamide.

5. A method for treating a disease in a subject comprising: administering to a subject a composition comprising a vinca alkaloid derivative, wherein the vinca alkaloid derivative is selected from a hydrazinolyzed vinca alkaloid and physiologically acceptable salts thereof, and a vinca alkaloid dipeptide derivative and physiologically acceptable salts thereof; wherein the hydrazinolyzed vinca alkaloid is JJ-CCXJ or JJ-CCFN shown as follows:

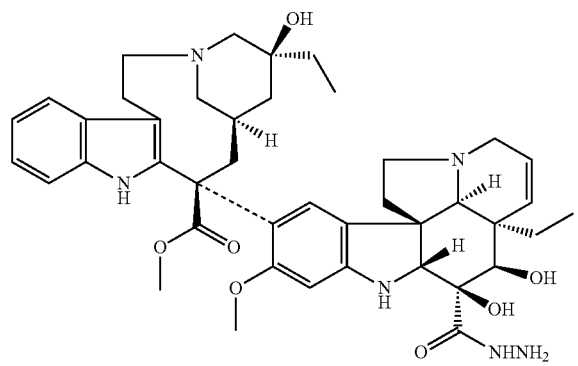

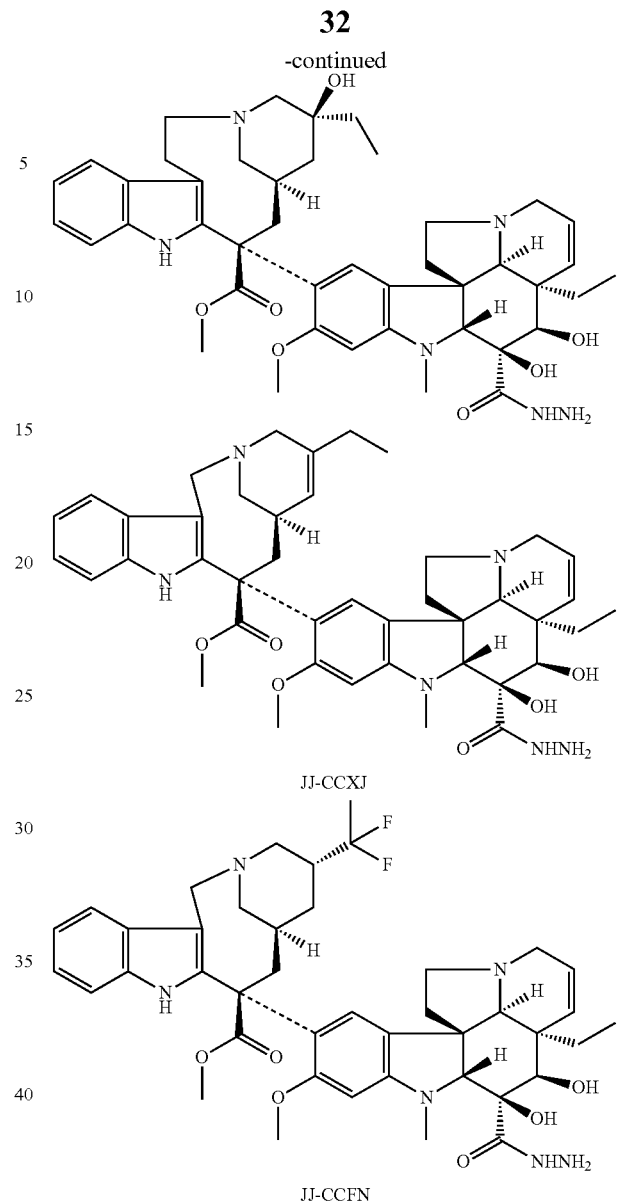

JJ-CCXJ

JJ-CCFN and wherein the vinca alkaloid dipeptide derivative is selected from the group consisting of BX-CCXJ, BX-CCJ, BX-CCRB and BX-CCFN shown as follows

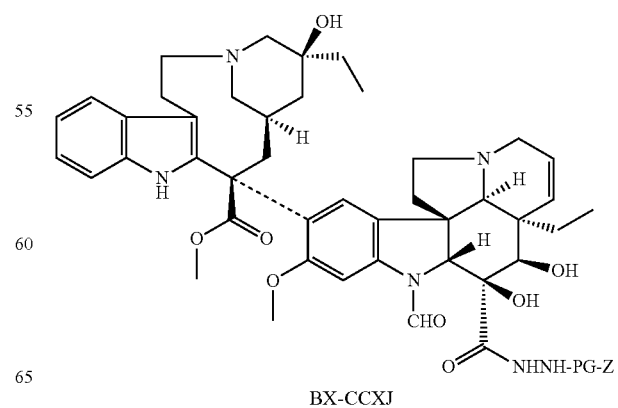

BX-CCXJ

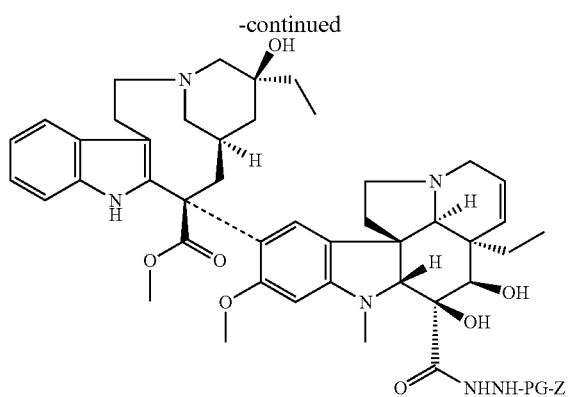

BX-CCJ

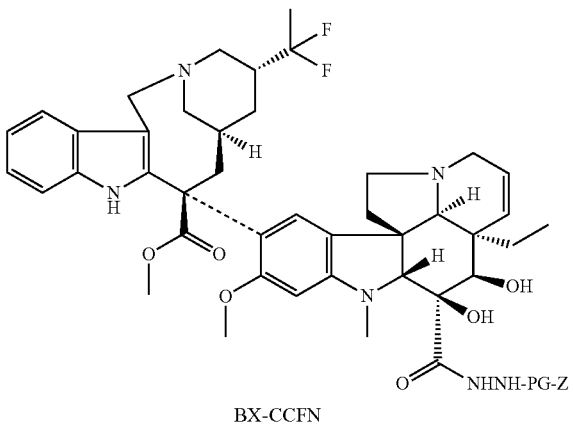

BX-CCRB

BX-CCFN wherein, -PG-Z represents a benzyloxycarbonylglycylprolyl group having the structure as follows

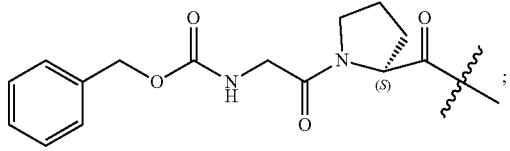

wherein the disease is a cancer selected from the group consisting of Hodgkin's lymphoma, non-Hodgkin's lymphoma, acute lymphoblastic leukemia, testicular cancer, non-small cell lung cancer, stomach cancer, nasopharyngeal cancer, breast cancer, intestinal cancer, liver cancer, leukemia, prostate cancer, cervical cancer, melanoma, ovarian cancer, neuroblastoma, nephroblastoma, rheumatoid arthritis, and diabetic retinopathy.

6. The method of claim 5, the vinca alkaloid dipeptide derivative or a physiologically acceptable salt thereof serves as a substrate for specific hydrolysis by tumor stroma fibroblast activating protease α (FAPα).

7. The method according to claim 5, wherein the physiologically acceptable salt is selected from hydrochloride, sulfate, acetate, tartrate and citrate.

8. The method according to claim 5, wherein the composition, serves as an angiogenesis inhibitor or a vascular disrupting agent.

9. The method according to claim 5, wherein the physiologically acceptable salt is selected from hydrochloride, sulfate, acetate, tartrate and citrate.

* * * * *